US012806301B2

(12) United States Patent
Hebrink et al.

(10) Patent No.: US 12,806,301 B2
(45) Date of Patent: Nov. 24, 2026

(54) ULTRAVIOLET-C EMITTING DISINFECTING DEVICE AND METHOD OF USING THE SAME

(71) Applicant: 3M INNOVATIVE PROPERTIES COMPANY, St. Paul, MN (US)

(72) Inventors: Timothy J. Hebrink, Scandia, MN (US); John A. Wheatley, Stillwater, MN (US); Bharat R. Acharya, Woodbury, MN (US); Tao Liu, Woodbury, MN (US); Stephen P. Maki, North St. Paul, MN (US); Gilles J.B. Benoit, Minneapolis, MN (US); Sean M. Sweetnam, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 539 days.

(21) Appl. No.: 18/257,716

(22) PCT Filed: Nov. 23, 2021

(86) PCT No.: PCT/IB2021/060889
§ 371 (c)(1),
(2) Date: Jun. 15, 2023

(87) PCT Pub. No.: WO2022/144625
PCT Pub. Date: Jul. 7, 2022

(65) Prior Publication Data

US 2024/0115746 A1 Apr. 11, 2024

Related U.S. Application Data

(60) Provisional application No. 63/132,830, filed on Dec. 31, 2020.

(51) Int. Cl.
*A61L 2/10* (2026.01)
*G02B 1/04* (2006.01)
(Continued)

(52) U.S. Cl.
CPC .................. *A61L 2/10* (2013.01); *G02B 1/04* (2013.01); *G02B 5/0891* (2013.01); *G02B 5/208* (2013.01);
(Continued)

(58) Field of Classification Search
CPC ........... A61L 2/10; G02B 1/04; G02B 5/0891; G02B 5/208; H01J 61/025; H01J 61/40
See application file for complete search history.

(56) References Cited

U.S. PATENT DOCUMENTS 5,504,134 A 4/1996 Palmer et al.
5,686,793 A 11/1997 Turner et al.
(Continued)

FOREIGN PATENT DOCUMENTS

CN 107670067 A 2/2018
DE 4302555 A1 7/1998
(Continued)

OTHER PUBLICATIONS

Berreman, "Optics is Stratified and Anisotropic Media: 4×4-Matrix Formulation", Journal of the Optical Society of America, 1972, vol. 62, No. 4, pp. 502-510.
(Continued)

*Primary Examiner* — Sean E Conley
(74) *Attorney, Agent, or Firm* — Lynn R. Hunsberger; Jonathan V. Sry

(57) ABSTRACT

A device including a housing that is substantially impermeable to ultraviolet radiation having a wavelength of from 280 nm to 400 nm, and at least one window defined in the housing, the window including a UV-C radiation band-pass mirror film having a multiplicity of alternating first and second optical layers collectively transmitting UV-C radiation at a wavelength from at least 100 nm to less than 280 nm and not transmitting UV-A and UV-B radiation at a
(Continued)

wavelength of from 280 nm to 400 nm, and an ultraviolet radiation source positioned within the housing, the ultraviolet radiation source being capable of emitting ultraviolet radiation at one or more wavelength from 100 nm to 400 nm. The device optionally further includes an ultraviolet mirror film positioned within the housing so as to reflect ultraviolet radiation emitted by the ultraviolet radiation source. A method of disinfecting a material is also disclosed.

14 Claims, 15 Drawing Sheets

(51) Int. Cl.
*G02B 5/08* (2006.01)
*G02B 5/20* (2006.01)
*H01J 61/02* (2006.01)
*H01J 61/40* (2006.01)

(52) U.S. Cl.
CPC ............ *H01J 61/025* (2013.01); *H01J 61/40* (2013.01); *A61L 2202/11* (2013.01)

(56) References Cited

U.S. PATENT DOCUMENTS

| | | | |
|---|---|---|---|
| 5,876,688 | A | 3/1999 | Laundon |
| 6,418,257 | B1 | 7/2002 | Nath |
| 6,447,537 | B1 | 9/2002 | Hartman |
| 6,449,093 | B2 | 9/2002 | Hebrink et al. |
| 6,744,561 | B2 | 6/2004 | Condo et al. |
| 6,783,349 | B2 | 8/2004 | Neavin et al. |
| 8,753,575 | B2 | 6/2014 | Neister |
| 8,921,813 | B2 | 12/2014 | Palmer et al. |
| 9,459,386 | B2 | 10/2016 | Hebrink et al. |
| 9,523,516 | B2 | 12/2016 | Hebrink et al. |
| 9,657,177 | B1 | 5/2017 | Pringle et al. |
| 9,696,467 | B2 | 7/2017 | Schreiber et al. |
| 10,786,586 | B2 | 9/2020 | Igarashi |
| 2004/0145288 | A1 | 7/2004 | Ouderkirk et al. |
| 2006/0084780 | A1 | 4/2006 | Hebrink et al. |
| 2011/0036390 | A1 | 2/2011 | Nelson et al. |
| 2011/0247686 | A1 | 10/2011 | Honeker et al. |
| 2012/0041122 | A1 | 2/2012 | Hidaka et al. |
| 2012/0227809 | A1 | 9/2012 | Bharti et al. |
| 2014/0083481 | A1 | 3/2014 | Hebrink et al. |
| 2015/0114912 | A1 | 4/2015 | Taghipour |
| 2016/0155902 | A1 | 6/2016 | Lunev et al. |
| 2017/0182194 | A1 | 6/2017 | Shin et al. |
| 2017/0216466 | A1 | 8/2017 | Dujowich et al. |
| 2017/0290934 | A1 | 10/2017 | Dobrinksy et al. |
| 2018/0201521 | A1 | 7/2018 | Taghipour |
| 2019/0298871 | A1 | 10/2019 | Dobrinsky |

FOREIGN PATENT DOCUMENTS

| | | | | |
|---|---|---|---|---|
| DE | 102014105478 | B3 | 7/2015 | |
| EP | 0521553 | B1 | 4/1996 | |
| JP | 2002-225192 | A | 8/2002 | |
| JP | 2017-209083 | A | 11/2017 | |
| WO | 2013066459 | A1 | 5/2013 | |
| WO | 2013066460 | A1 | 5/2013 | |
| WO | 2014007212 | A1 | 1/2014 | |
| WO | 2014022049 | A1 | 2/2014 | |
| WO | 2017172564 | A2 | 10/2017 | |
| WO | WO-2020136557 | A1 * | 7/2020 | ................ C02F 1/32 |

OTHER PUBLICATIONS

Davis, "Model of magnetorheological elastomers", Journal of Applied Physics, Mar. 1999, vol. 85, No. 6, pp. 3348-3351.

Dohring, "Critical discussion on the UV absorption properties of Earth's atmosphere", Proceedings of the SPIE, Aug. 2017, vol. 10453, 10 pages,.

Frieden, "Restoring with Maximum Likelihood and Maximum Entropy", Journal of the Optical Society of America, Apr. 1972, vol. 62, No. 4, pp. 511-518.

International Search Report for PCT Application No. PCT/IB2020/062460 mailed on Jun. 17, 2021, 7 pages.

International Search Report for PCT International Application No. PCT/IB21/60889, mailed on Feb. 4, 2022, 3 pages.

Kitamura, "A Practical High-Power Excimer Lamp Excited by a Microwave Discharge", Applied Surface Science, 1994, vol. 79/80, pp. 507-513.

Kogelschatz, "Silent-Discharge Driven Excimer UV Sources and Their Applications", Applied Surface Science, 1992, vol. 54, pp. 410-423.

MatWeb Overview of materials for Ethylene Vinyl Acetate Copolymer (EVA), Adhesive/Sealant Grade, 2023, pp. 1-2.

Stallinga, "Berreman 4x4 matrix method for reflective liquid crystal displays", Journal of Applied Physics, Mar. 15, 1999, vol. 85, No. 6, pp. 3023-3031.

* cited by examiner

ULTRAVIOLET-C EMITTING DISINFECTING DEVICE AND METHOD OF USING THE SAME

CROSS REFERENCE TO RELATED APPLICATIONS

This application is a national stage filing under 35 U.S.C. 371 of PCT/IB2021/060889, filed Nov. 23, 2021, which claims the benefit of U.S. Provisional Patent Application No. 63/132,830, filed Dec. 31, 2020, the disclosure of which is incorporated by reference in its/their entirety herein.

BACKGROUND

Ultraviolet (UV) light or radiation is useful, for example, in initiating free radical chemical reactions used in producing coatings, adhesives, and various (co)polymeric materials. Ultraviolet radiation also may be useful, for example, in disinfecting surfaces, such as bandages, membranes, and filtration media, and for disinfection of air and liquids (e.g., water). Air and water disinfection is paramount to human health and preventing infectious diseases. Prevention of infection and spread of disease, especially in high-risk environments and populations, has become increasingly more important as pathogens mutate and develop antibiotic resistance.

Hospitals are currently disinfecting patient rooms, operating rooms and hospital surfaces using harsh chemicals that may have annoying odors and undesirable health effects. Public restrooms also have well known disease carrying and bacteria transferring surfaces and are commonly disinfected using chemical disinfection methods. In addition to hospital rooms and public restrooms, other public areas, including public transportation such as buses, trains and airplanes, as well as public schools, restaurants, grocery and retail stores, all require periodic disinfection to prevent the spread of disease. The availability and speed of global human travel elevates risks of rapidly spreading diseases on surfaces that are not regularly nondisinfected, which can lead to disease epidemics or even pandemics.

UV-C radiation (i.e., electromagnetic radiation emissions at one or more wavelengths in a range from 100 nanometers to 280 nanometers) can be used to effectively inactivate or kill prokaryotic and eukaryotic microorganisms alike, including bacteria, viruses, spores, fungi and molds. Bacterial strains with developed resistance to one or more antibiotics nevertheless remain susceptible to the effects of UV-C radiation exposure. Some examples of pathogens of particular interest for application of UV-C irradiation disinfection include hospital acquired infections (e.g., *C. diff, E. coli*, Methicillin Resistant *Staphylococcus aureus* [MRSA], *Klebsiella*, influenza, mycobacteria, and enterobacteria), water and soil borne infections (e.g., *Giardia, Legionella*, and *Campylobacter*) and airborne infections (e.g., influenza, pneumonia, and tuberculosis).

SUMMARY

UV radiation emitted at some specific wavelengths can be harmful to people and animals to varying degrees. Unfortunately, many commercially available ultraviolet radiation sources capable of emitting UV-C radiation useful in achieving disinfection also emit UV-A radiation (i.e., electromagnetic radiation emissions at one or more wavelengths in a range from 315 nanometers to 400 nanometers) and/or UV-B radiation (i.e., electromagnetic radiation emissions at one or more wave-lengths in a range from 280 nanometers to 315 nanometers). While UV-A and UV-B radiation differ in how they affect the skin, they both can do harm. Unprotected extended exposure to UV-A and UV-B radiation can damage the DNA in human skin cells, producing genetic defects, or mutations that can lead to premature aging, wrinkling and even skin cancer, as well as eye damage, for example cataracts and eyelid cancers.

Accordingly, the present disclosure relates to disinfection devices which incorporate low cost, commercially available broadband UV light sources, but which incorporate one or more multilayer UV-C mirror films which act as a band-pass filter that can transmit a substantial amount of UV-C radiation which is useful in disinfection, and reflect substantially all of the UV-A and UV-B radiation which can have undesirable health effects. Such devices are particularly useful in portable or hand-held disinfection applications because the UV-C radiation emitted by the disinfection device can be used to in the presence of human beings and animals without causing significant adverse health effects.

Thus, in one aspect, the present disclosure describes a device including a housing that is substantially impermeable to ultraviolet radiation having a wavelength of from 280 nm to 400 nm, and at least one window defined in the housing, and an ultraviolet radiation source positioned within the housing. The ultraviolet radiation source is capable of emitting ultraviolet radiation at one or more wavelength from 100 nm to 400 nm. The window includes a UV-C radiation band-pass mirror film including a multiplicity of alternating first and second optical layers collectively transmitting UV-C radiation at a wavelength from at least 100 nm, 125 nm, 150 nm, 160 nm, 170 nm, 180 nm or 190 nm, to less than 280 nm, 270 nm, 260 nm, 250 nm, 240 nm, or 230 nm. The UV-C radiation band-pass mirror film does not substantially transmit UV-A and UV-B radiation at a wavelength of from 280 nm to 400 nm.

The present disclosure also describes multilayer UV-C mirror films which can be used within the UV radiation impermeable housing of a disinfecting device to reflect UV-C radiation from the broadband UV light source to a window in the disinfecting device covered with the multilayer UV-C mirror film acting as a band-pass filter to allow emission of a substantial amount of the UV-C radiation useful in disinfection of surfaces while reflecting substantially all of the UV-A and UV-B radiation which can have undesirable health effects back into the housing.

Thus, in some particularly advantageous embodiments, the device further includes an ultraviolet mirror film positioned within the housing so as to reflect ultraviolet radiation emitted by the ultraviolet radiation source. The ultraviolet mirror film includes a multiplicity of alternating first and second optical layers collectively reflecting at least 50, 60, 70, 80, 90, or 95 percent of incident UV-C ultraviolet radiation in a wavelength range from at least 100 nm, 125 nm, 150 nm, 160 nm, 170 nm, 180 nm, 190 nm, or 200 nm, to 400 nm, 300 nm, 280 nm, 270 nm, 260 nm, 250 nm, 240 nm or 230 nm, and collectively transmitting at least 50, 60, 70, 80, 90, or 95 percent of incident ultraviolet radiation in a wavelength range from greater than 230 nanometers, greater than 235 nm, or greater than 240 nm, to 400 nanometers. At least 50, 60, 70, 80, 90, or 95 percent of the ultraviolet radiation having a wavelength between at least 230 nanometers and 400 nanometers transmitted through the ultraviolet mirror is absorbed by the ultraviolet mirror film.

Furthermore, because some surfaces (e.g., (co)polymeric surfaces) being disinfected with ultraviolet radiation may need protection from even UV-C ultra-violet light, the present disclosure also relates to UV-C mirror protection films which can reflect UV-C radiation and optionally one or more of UV-A and UV-B radiation, thereby protecting an underlying surface to which the UV mirror protection film has been applied from damage due to the effects of UV irradiation exposure.

Thus, in another aspect, the present disclosure describes UV-C mirror films including a substrate comprised of a fluoropolymer; a multilayer optical film disposed on a major surface of the substrate, wherein the multilayer optical film is comprised of at least a plurality of alternating first and second optical layers collectively reflecting at an incident light angle of at least one of 0°, 30°, 45°, 60°, or 75°, at least 30 percent of incident ultraviolet radiation over at least a 30-nanometer wavelength reflection bandwidth in a wavelength range from at least 100 nanometers to 280 nanometers or optionally in a wavelength range from at least 240 nm to 400 nm; and a heat-sealable adhesive layer disposed on a major surface of the multilayer optical film opposite the substrate.

In any of the foregoing embodiments, the fluoropolymer is a (co)polymer comprising tetrafluoroethylene, hexafluoropropylene, vinylidene fluoride, a perfluoroalkoxy alkane, or a combination thereof. In some such embodiments, the heat-sealable adhesive layer comprises a (co)polymer. In any of the foregoing embodiments, the (co)polymer is selected from an olefinic (co)polymer, a (meth)acrylate (co)polymer, a urethane (co)polymer, a fluoropolymer, a silicone (co)polymer, or a combination thereof. In certain such embodiments, the (co)polymer is an olefinic (co) polymer selected from low density polyethylene, linear low density polyethylene, ethylene vinyl acetate, polyethylene methyl acrylate, polyethylene octene, polyethylene propylene, polyethylene butene, polyethylene maleic anhydride, polymethyl pentene, polyisobutene, polyisobutylene, polyethylene propylene diene, cyclic olefin copolymers, and blends thereof.

In some of the foregoing UV-C mirror film embodiments, the (co)polymer has a melting temperature in the range of 110 C to 190 C. In other exemplary embodiments, the (co)polymer has a melting temperature less than 150° C. In certain such embodiments, the (co)polymer is crosslinked. In some such embodiments, the (co)polymer further comprises an ultraviolet radiation absorber, a hindered amine light stabilizer, an antioxidant, or a combination thereof. In further such embodiments, the ultraviolet radiation absorber is selected from a benzotriazole compound, a benzophenone compound, a triazine compound, or a combination thereof.

In any of the foregoing UV-C mirror film embodiments, the at least first optical layer comprises at least one polyethylene (co)polymer, and wherein the second optical layer comprises at least one fluoropolymer selected from a tetrafluoroethylene (co)polymer, a hexafluoropropylene (co) polymer, a vinylidene fluoride (co)polymer, a hexafluoropropylene (co)polymer, a perfluoroalkoxy alkane (co) polymer, or a combination thereof. In some such embodiments, the at least one fluoropolymer is crosslinked.

In any of the foregoing embodiments, the at least first optical layer comprises at least one of zirconium oxynitride, hafnia, alumina, magnesium oxide, yttrium oxide, lanthanum fluoride, or neodymium fluoride, and wherein the second optical layer comprises at least one of silica, aluminum fluoride, magnesium fluoride, calcium fluoride, silica alumina oxide or alumina doped silica.

In another aspect, the present disclosure describes a method of using a disinfection device according to any of the foregoing device embodiments to disinfect a surface to a desired degree of disinfection, the method including providing the disinfecting device; directing ultraviolet radiation emitted by the ultraviolet radiation source through the UV-C band-pass mirror film; and exposing the at least one material to the ultraviolet radiation passing through the UV-C band-pass mirror film for a time sufficient to achieve a desired degree of disinfection of the at least one material. The ultraviolet radiation passing through the UV-C band-pass mirror film is in a wavelength range from at least 100 nm, 125 nm, 150 nm, 160 nm, 170 nm, 180 nm or 190 nm, to less than 280 nm, 270 nm, 260 nm, 250 nm, 240 nm, or 230 nm. The ultraviolet light passing through the UV-C band-pass filter does not substantially include UV-A and UV-B radiation at a wavelength of from 280 nm to 400 nm.

In some presently preferred embodiments, exposing the at least one material to the ultraviolet radiation passing through the UV-C band-pass mirror film for a time sufficient to achieve a desired degree of disinfection of the at least one material achieves a log 2, log 3, log 4, or greater reduction in an amount of at least one microorganism present on or in the at least one material, as compared to an amount of the at least one microorganism present prior to exposing the at least one material to the ultraviolet radiation passing through the UV-C band-pass mirror film.

Various unexpected results and advantages are obtained in various exemplary embodiments of the disclosure, a partial listing of which follows.

LISTING OF EXEMPLARY EMBODIMENTS

Embodiment A: A device comprising:

- a housing that is substantially impermeable to ultraviolet radiation having a wavelength of from 280 nm to 400 nm, and at least one window defined in the housing, wherein the window comprises a UV-C radiation band-pass mirror film comprised of a plurality of alternating first and second optical layers collectively transmitting UV-C radiation at a wavelength from at least 100 nm, 125 nm, 150 nm, 160 nm, 170 nm, 180 nm or 190 nm, to less than 280 nm, 270 nm, 260 nm, 250 nm, 240 nm, or 230 nm and does not substantially transmit UV-A and UV-B radiation at a wavelength of from 280 nm to 400 nm; and
- an ultraviolet radiation source positioned within the housing, wherein the ultraviolet radiation source is capable of emitting ultraviolet radiation at one or more wavelength from 100 nm to 400 nm; the device optionally further comprising:
- an ultraviolet mirror film positioned within the housing so as to reflect ultraviolet radiation emitted by the ultraviolet radiation source, wherein the ultraviolet mirror film is comprised of at least a plurality of alternating first and second optical layers collectively reflecting at least 50, 60, 70, 80, 90, or 95 percent of incident UV-C ultraviolet radiation in a wavelength range from at least 100 nm, 125 nm, 150 nm, 160 nm, 170 nm, 180 nm, 190 nm, or 200 nm, to 400 nm, 300 nm, 280 nm, 270 nm, 260 nm, 250 nm, 240 nm or 230 nm, and collectively transmitting at least 50, 60, 70, 80, 90, or 95 percent of incident ultraviolet radiation in a wavelength range from greater than 230 nanometers, greater than 235 nm, or greater than 240 nm, to 400 nanometers, \wherein at least 50, 60, 70, 80, 90, or 95 percent of ultraviolet radiation having a wavelength between at least 230 nanometers and 400 nanometers transmitted through the ultraviolet mirror is absorbed in the chamber.

Embodiment B: The device of Embodiment A, wherein the housing comprises a hollow nonplanar shape, further wherein the ultraviolet radiation source is substantially surrounded by the housing.

Embodiment C: The device of any preceding Embodiment, wherein the ultraviolet radiation source is a germicidal lamp, or an excimer lamp.

Embodiment D: The device of any preceding Embodiment, wherein the UV-C radiation band-pass mirror film comprises at least a first optical layer comprising at least one of zirconium oxynitride, hafnia, alumina, magnesium oxide, yttrium oxide, lanthanum fluoride, or neodymium fluoride and at least a second optical layer comprising at least one of silica, aluminum fluoride, magnesium fluoride, calcium fluoride, silica alumina oxide, or alumina doped silica.

Embodiment E: The device of Embodiment D, wherein the at least first optical layer comprises at least one of polyvinylidene fluoride or polyethylene tetrafluoroethylene and wherein the at least second optical layer comprises fluorinated ethylene propylene (FEP) or a copolymer of tetrafluoroethylene, hexafluoropropylene, and vinylidene fluoride.

Embodiment F: The device of any preceding Embodiment, wherein the ultraviolet mirror film is positioned within the housing.

Embodiment G: The device of Embodiment F, wherein the ultraviolet mirror film is separated from the ultraviolet radiation source by an air gap.

Embodiment H: The device of Embodiment F or G, wherein the ultraviolet mirror film comprises:

a substrate comprised of a fluoropolymer;

a multilayer optical film disposed on a major surface of the substrate, wherein the multilayer optical film is comprised of at least a plurality of alternating first and second optical layers collectively reflecting incident ultraviolet radiation over at least a 30-nanometer wavelength reflection bandwidth in a wavelength range from at least 100 nanometers to 400 nanometers or optionally in a wavelength range from at least 180 to less than 280 nm; and optionally an adhesive layer disposed on a major surface of the ultraviolet mirror film.

Embodiment I: The device of Embodiment H, wherein the fluoropolymer is a (co)polymer comprising tetrafluoroethylene, hexafluoropropylene, vinylidene fluoride, a perfluoroalkoxy alkane, or a combination thereof.

Embodiment J: The device of Embodiments H or I, wherein the at least first optical layer of the multilayer optical film comprises at least one polyethylene (co) polymer, and wherein the second optical layer comprises at least one fluoropolymer selected from a tetrafluoroethylene (co)polymer, a hexafluoropropylene (co)polymer, a vinylidene fluoride (co)polymer, a hexafluoropropylene (co)polymer, a perfluoroalkoxy alkane (co)polymer, or a combination thereof, optionally wherein the at least one fluoropolymer is crosslinked.

Embodiment K: The device of Embodiments H, I or J, wherein the at least first optical layer of the multilayer optical film comprises at least one of zirconium oxynitride, hafnia, alumina, magnesium oxide, yttrium oxide, lanthanum fluoride, or neodymium fluoride and wherein the second optical layer comprises at least one of silica, aluminum fluoride, magnesium fluoride, calcium fluoride, silica alumina oxide or alumina doped silica.

Embodiment L: The device of Embodiments H, I, J or K, wherein the at least first optical layer of the multilayer optical film comprises at least one of polyvinylidene fluoride or polyethylene tetrafluoroethyne and wherein the second optical layer comprises a copolymer of tetrafluoroethylene, hexafluoropropylene, and vinylidene fluoride.

Embodiment M: The device of Embodiments H, I, J, K or L, wherein the adhesive layer is present and positioned adjacent to the housing, further wherein the adhesive layer comprises a (co)polymer.

Embodiment N: The device of Embodiment M, wherein the adhesive layer further comprises an ultraviolet radiation absorber selected from a benzotriazole compound, a benzophenone compound, a triazine compound, or a combination thereof.

Embodiment O: A method of disinfecting at least one material, the method comprising:

providing the device of any of Embodiments A, B, C, D, E, F, G, H, I, J, K, L, M or N;

directing ultraviolet radiation emitted by the ultraviolet radiation source through the UV-C band pass mirror film; and exposing the at least one material to the ultraviolet radiation passing through the UV-C band pass mirror film for a time sufficient to achieve a desired degree of disinfection of the at least one material, wherein the ultraviolet radiation passing through the UV-C band-pass mirror film is in a wavelength range from at least 100 nm, 125 nm, 150 nm, 160 nm, 170 nm, 180 nm or 190 nm, to less than 280 nm, 270 nm, 260 nm, 250 nm, 240 nm, or 230 nm, and does not substantially include UV-A and UV-B radiation at a wavelength of from 280 nm to 400 nm, optionally wherein exposing the at least one material to the ultraviolet radiation passing through the UV-C band-pass mirror film is performed until achievement of a log 2, log 3, log 4, or greater reduction in an amount of at least one microorganism present on or in the at least one material, as compared to an amount of the at least one microorganism present prior to exposing the at least one material to the ultraviolet radiation passing through the UV-C band-pass mirror film.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

Figure 1:
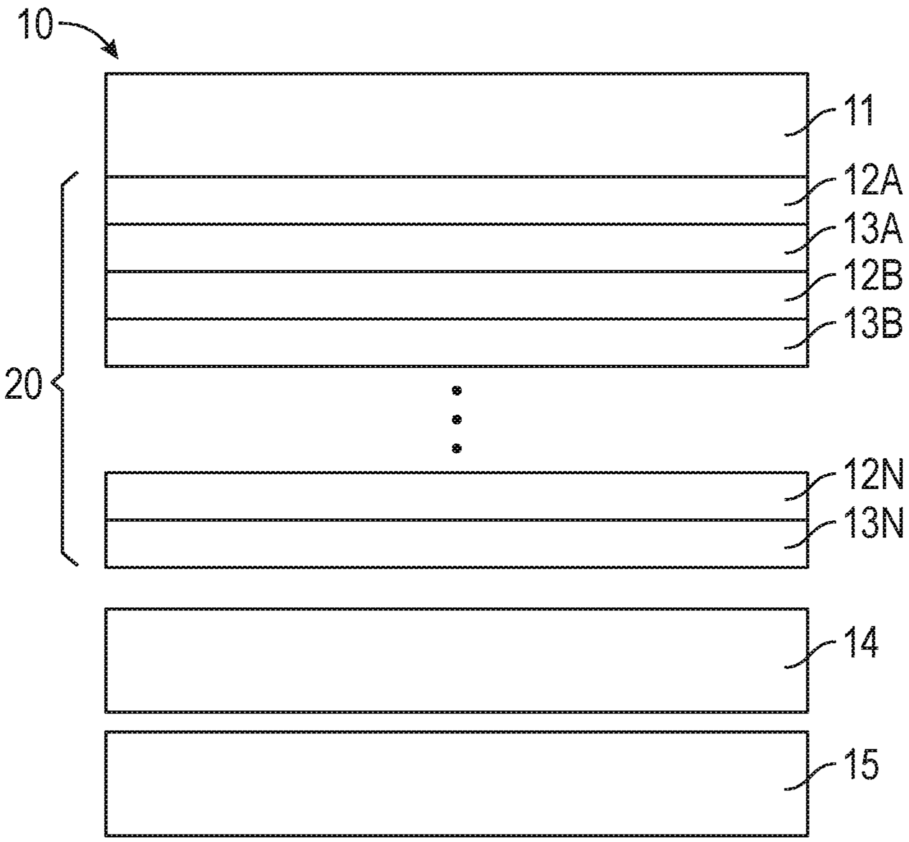
FIG. 1 is a schematic cross-sectional view of an exemplary multilayer optical film used in exemplary assemblies described herein.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

For the following Glossary of defined terms, these definitions shall be applied for the entire application, unless a different definition is expressly provided in the claims or elsewhere in the specification.

Glossary

The terms "(co)polymer" or "(co)polymers" includes homopolymers and copolymers, as well as homopolymers or copolymers that may be formed in a miscible blend, e.g., by coextrusion or by reaction, including, e.g., transesterification. The term "copolymer" includes random, block and star (e.g. dendritic) copolymers.

The term "(meth)acryl" or "(meth)acrylate" with respect to a monomer, oligomer or means a vinyl-functional alkyl ester formed as the reaction product of an alcohol with an acrylic or a methacrylic acid.

The term "fluoropolymer" refers to any organic (co) polymer containing fluorine.

The term "SPDX" means a silicone poloxamide (co) polymer,

The term "incident" with respect to light refers to the light falling on or striking a material.

The term "radiation" refers to electromagnetic radiation unless otherwise specified.

The term "absorption" refers to a material converting the energy of light radiation to internal energy.

The term "absorb" with respect to wavelengths of light encompasses both absorption and scattering, as scattered light also eventually gets absorbed.

The term "scattering" with respect to wavelengths of light refers to causing the light to depart from a straight path and travel in different directions with different intensities.

The term "reflectance" is the measure of the proportion of light or other radiation striking a surface at normal incidence which is reflected off it. Reflectivity typically varies with wavelength and is reported as the percent of incident light that is reflected from a surface (0 percent—no reflected light, 100—all light reflected. Reflectivity and reflectance are used interchangeably herein.

The term "reflective" and "reflectivity" refer to the property of reflecting light or radiation, especially reflectance as measured independently of the thickness of a material.

The term "average reflectance" refers to reflectance averaged over a specified wavelength range.

The term "absorbance" with respect to a quantitative measurement refers to the base 10 logarithm of a ratio of incident radiant power to transmitted radiant power through a material. The ratio may be described as the radiant flux received by the material divided by the radiant flux transmitted by the material. Absorbance (A) may be calculated based on transmittance (T) according to Equation 1:

$$A=-\log_{10}T \quad (1)$$

Absorbance can be measured with methods described in ASTM E903-12 "Standard Test Method for Solar Absorptance, Reflectance, and Transmittance of Materials Using Integrating Spheres". Absorbance measurements described herein were made by making transmission measurements as previously described and then calculating absorbance using Equation (1). Emissivity can be measured using infrared imaging radiometers with methods described in ASTM E1933-14 (2018) "Standard Practice for Measuring and Compensating for Emissivity Using Infrared Imaging Radiometers."

The term or prefix "micro" refers to at least one dimension defining a structure or shape being in a range from 1 micrometer to 1 millimeter. For example, a micro-structure may have a height or a width that is in a range from 1 micrometer to 1 millimeter.

The term or prefix "nano" refers to at least one dimension defining a structure or a shape being less than 1 micrometer. For example, a nano-structure may have at least one of a height or a width that is less than 1 micrometer.

The term "adjoining" with reference to a particular layer means joined with or attached to another layer, in a position wherein the two layers are either next to (i.e., adjacent to) and directly contacting each other, or contiguous with each other but not in direct contact (i.e., there are one or more additional layers intervening between the layers).

By using terms of orientation such as "atop", "on", "over," "covering", "uppermost", "underlying" and the like for the location of various elements in the disclosed coated articles, we refer to the relative position of an element with respect to a horizontally-disposed, upwardly-facing substrate. However, unless otherwise indicated, it is not intended that the substrate or articles should have any particular orientation in space during or after manufacture.

By using the term "overcoated" to describe the position of a layer with respect to a substrate or other element of an article of the present disclosure, we refer to the layer as being atop the substrate or other element, but not necessarily contiguous to either the substrate or the other element.

By using the term "separated by" to describe the position of a layer with respect to other layers, we refer to the layer as being positioned between two other layers but not necessarily contiguous to or adjacent to either layer.

The terms "about" or "approximately" with reference to a numerical value or a shape means +/− five percent of the numerical value or property or characteristic, but expressly includes the exact numerical value. For example, a viscosity of "about" 1 Pa-sec refers to a viscosity from 0.95 to 1.05 Pa-sec, but also expressly includes a viscosity of exactly 1 Pa-sec. Similarly, a perimeter that is "approximately square" is intended to describe a geometric shape having four lateral edges in which each lateral edge has a length which is from 99% to 101% of the length of any other lateral edge, but which also includes a geometric shape in which each lateral edge has exactly the same length.

The term "substantially" with reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

As used in this specification and the appended embodiments, the singular forms "a", "an", and "the" include plural referents unless the content clearly dictates otherwise. Thus, for example, reference to fine fibers containing "a compound" includes a mixture of two or more compounds. As used in this specification and the appended embodiments, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

By definition, the total weight percentages of all ingredients in a composition equals 100 weight percent.

Various exemplary embodiments of the disclosure will now be described. Exemplary embodiments of the present disclosure may take on various modifications and alterations without departing from the spirit and scope of the present disclosure. Accordingly, it is to be understood that the embodiments of the present disclosure are not to be limited to the following described exemplary embodiments but is to be controlled by the limitations set forth in the claims and any equivalents thereof.

Ultraviolet-C Emitting Disinfecting Devices

Figure 9:
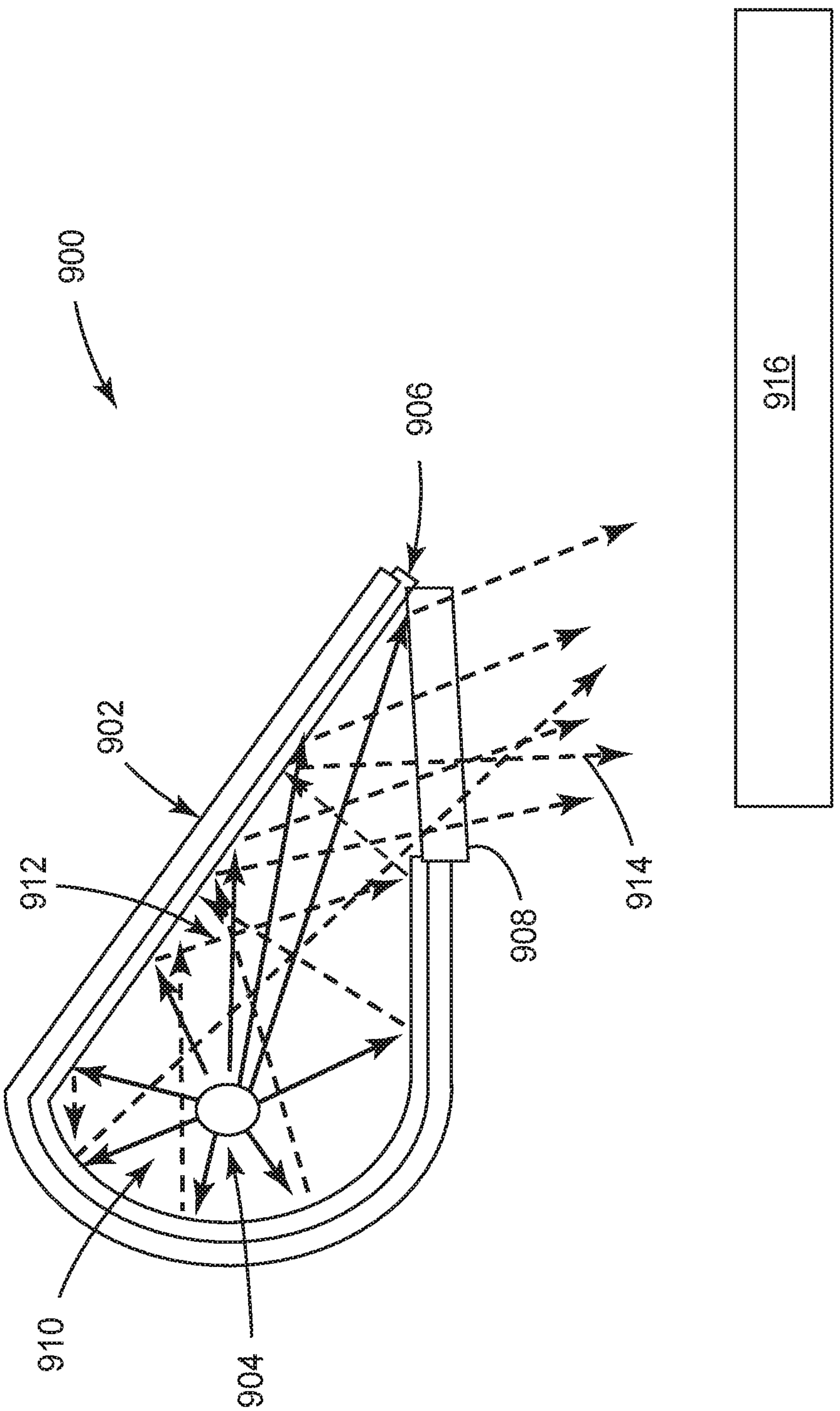
FIG. 9 is a schematic side view of a UV-C disinfecting device according to an exemplary embodiment of the present disclosure.

Turning now to the drawings, FIG. 9 shows a schematic side view of a device, more specifically a UV-C disinfecting device 900 according to an exemplary embodiment of the present disclosure. The device 900 comprising a housing 902 that is substantially impermeable to ultraviolet radiation having a wavelength of from 280 nm to 400 nm, at least one window 908 defined in the housing, and an ultraviolet radiation source 904 positioned within the housing. The ultraviolet radiation source 904 is capable of emitting ultraviolet radiation 910 at one or more wavelength from 100 nm to 400 nm.

The window 908 comprises a UV-C radiation band-pass mirror film including a multiplicity of alternating first and second optical layers collectively transmitting UV-C radiation 914 at a wavelength from at least 100 nm, 125 nm, 150 nm, 160 nm, 170 nm, 180 nm or 190 nm, to less than 280 nm, 270 nm, 260 nm, 250 nm, 240 nm, or 230 nm. The UV-C radiation band-pass mirror film does not substantially transmit UV-A and UV-B radiation at a wavelength of from 280 nm to 400 nm. The UV-C radiation emitted from the device may be directed at a material 916 to be disinfected to a desired level of disinfection.

In some particularly advantageous embodiments, the device 900 further includes an ultraviolet mirror film 906 positioned within the housing 902 so as to reflect 912 ultraviolet radiation 910 emitted by the ultraviolet radiation source 904. The ultraviolet mirror film 906 (see FIG. 1) includes a multiplicity of alternating first and second optical layers collectively reflecting at least 50, 60, 70, 80, 90, or 95 percent of incident UV-C ultraviolet radiation in a wavelength range from at least 100 nm, 125 nm, 150 nm, 160 nm, 170 nm, 180 nm, 190 nm, or 200 nm, to 400 nm, 300 nm, 280 nm, 270 nm, 260 nm, 250 nm, 240 nm or 230 nm, and collectively transmitting at least 50, 60, 70, 80, 90, or 95 percent of incident ultraviolet radiation in a wavelength range from greater than 230 nanometers, greater than 235 nm, or greater than 240 nm, to 400 nanometers. At least 50, 60, 70, 80, 90, or 95 percent of the ultraviolet radiation having a wavelength between at least 230 nanometers and 400 nanometers transmitted through the ultraviolet mirror is absorbed by the ultraviolet mirror film.

Figure 10:
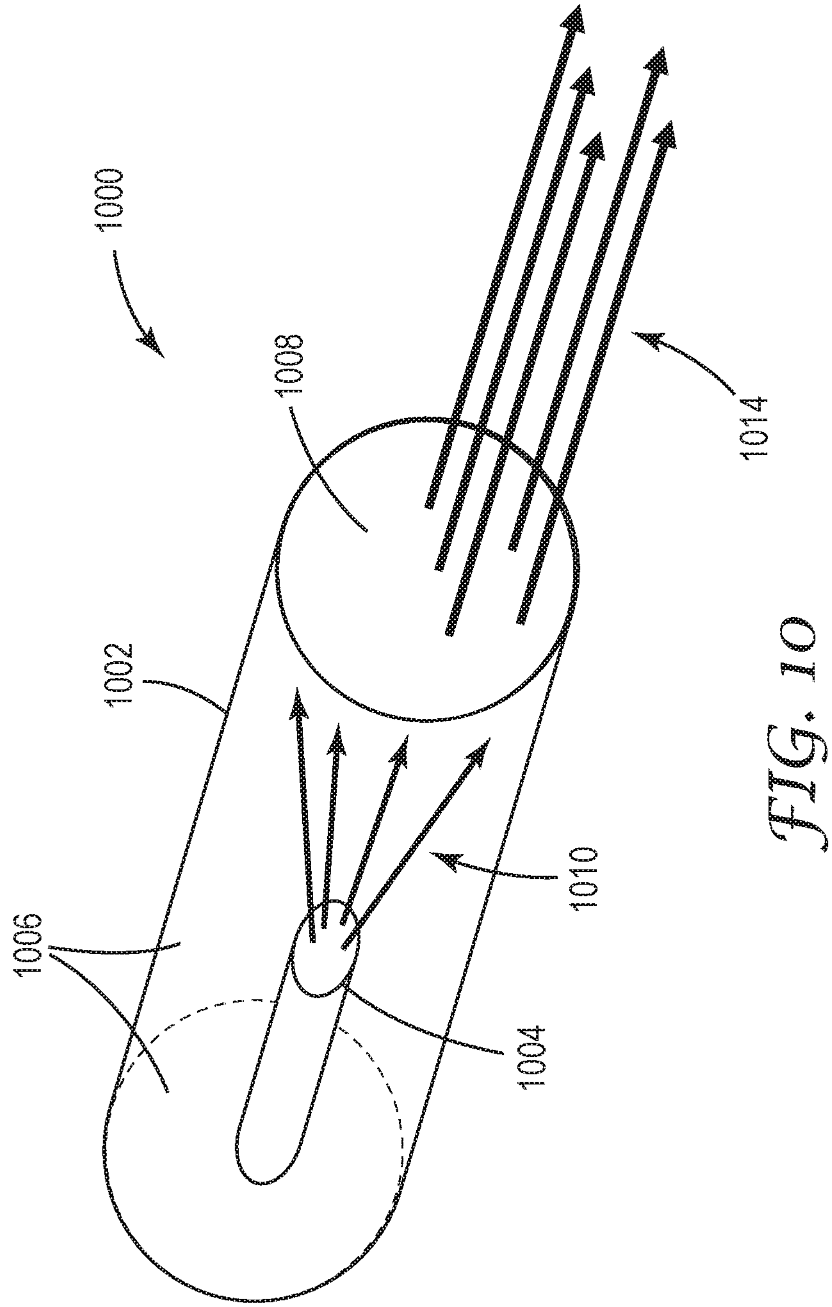
FIG. 10 is a schematic perspective view of another UV-C disinfecting device according to an exemplary embodiment of the present disclosure.

FIG. 10 is a schematic perspective view of another UV-C disinfecting device 1000 according to an exemplary embodiment of the present disclosure. The device 1000 comprises a housing 1002, that is substantially impermeable to ultraviolet radiation having a wavelength of from 280 nm to 400 nm, at least one window 1008 defined in the housing, and an ultraviolet radiation source 1004 positioned within the housing. The ultraviolet radiation source 1004 is capable of emitting ultraviolet radiation 1010 at one or more wavelength from 100 nm to 400 nm.

The window 1008 comprises a UV-C radiation band-pass mirror film including a multiplicity of alternating first and second optical layers collectively transmitting UV-C radiation 1014 at a wavelength from at least 100 nm, 125 nm, 150 nm, 160 nm, 170 nm, 180 nm or 190 nm, to less than 280 nm, 270 nm, 260 nm, 250 nm, 240 nm, or 230 nm. The UV-C radiation band-pass mirror film does not substantially transmit UV-A and UV-B radiation at a wavelength of from 280 nm to 400 nm. The UV-C radiation emitted from the device 1014 may be directed at a material (not shown) to be disinfected to a desired level of disinfection.

In some particularly advantageous embodiments, the device 1000 further includes an ultraviolet mirror film 1006 positioned within the housing 1002 so as to reflect ultraviolet radiation 1010 emitted by the ultraviolet radiation source 1004. The ultraviolet mirror film 1006 (see FIG. 1) includes a multiplicity of alternating first and second optical layers collectively reflecting at least 50, 60, 70, 80, 90, or 95 percent of incident UV-C ultraviolet radiation in a wavelength range from at least 100 nm, 125 nm, 150 nm, 160 nm, 170 nm, 180 nm, 190 nm, or 200 nm, to 400 nm, 300 nm, 280 nm, 270 nm, 260 nm, 250 nm, 240 nm or 230 nm, and collectively transmitting at least 50, 60, 70, 80, 90, or 95 percent of incident ultraviolet radiation in a wavelength range from greater than 230 nanometers, greater than 235 nm, or greater than 240 nm, to 400 nanometers. At least 50, 60, 70, 80, 90, or 95 percent of the ultraviolet radiation having a wavelength between at least 230 nanometers and 400 nanometers transmitted through the ultraviolet mirror is absorbed by the ultraviolet mirror film.

For the particular embodiment shown in FIG. 10, the window 1006 includes an optional collimator to cause the directions of motion of the emitted UV-C radiation 1014 to become more aligned in a specific direction (i.e., to produce collimated light having parallel rays). Suitable collimators are known to those skilled in the art, and include, for example, those described in U.S. Pat. Pub. Nos. 2015/0114912 A1 and 2018/0201521 A1.

Figure 11:
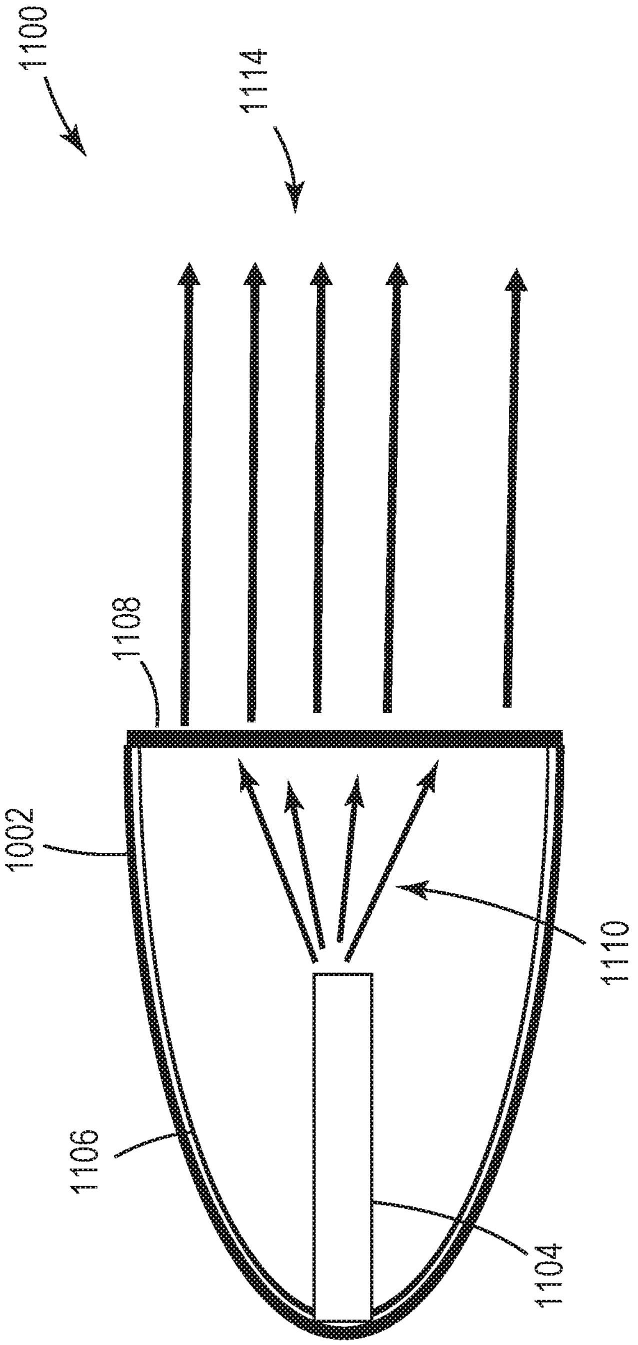
FIG. 11 is a schematic side view of a further UV-C disinfecting device using a collimated broadband UV light source according to another exemplary embodiment of the present disclosure.

FIG. 11 is a schematic side view of a further UV-C disinfecting device 1100 using a collimated broadband UV light source according to another exemplary embodiment of the present disclosure. The device 1100 comprises a housing 1102, that is substantially impermeable to ultraviolet radiation having a wavelength of from 280 nm to 400 nm, at least one window 1108 defined in the housing, and an ultraviolet radiation source 1104 positioned within the housing. The ultraviolet radiation source 1104 is capable of emitting ultraviolet radiation 1110 at one or more wavelength from 100 nm to 400 nm.

The window 1108 comprises a UV-C radiation band-pass mirror film including a multiplicity of alternating first and second optical layers collectively transmitting UV-C radiation 1114 at a wavelength from at least 100 nm, 125 nm, 150 nm, 160 nm, 170 nm, 180 nm or 190 nm, to less than 280 nm, 270 nm, 260 nm, 250 nm, 240 nm, or 230 nm. The UV-C radiation band-pass mirror film does not substantially transmit UV-A and UV-B radiation at a wavelength of from 280 nm to 400 nm. The UV-C radiation emitted from the device 1114 may be directed at a material (not shown) to be disinfected to a desired level of disinfection.

In some particularly advantageous embodiments, the device 1100 further includes an ultraviolet mirror film 1106 positioned within the housing 1102 so as to reflect ultraviolet radiation 1110 emitted by the ultraviolet radiation source 1104. The ultraviolet mirror film 1106 (see FIG. 1) includes a multiplicity of alternating first and second optical layers collectively reflecting at least 50, 60, 70, 80, 90, or 95 percent of incident UV-C ultraviolet radiation in a wavelength range from at least 100 nm, 125 nm, 150 nm, 160 nm, 170 nm, 180 nm, 190 nm, or 200 nm, to 400 nm, 300 nm, 280 nm, 270 nm, 260 nm, 250 nm, 240 nm or 230 nm, and collectively transmitting at least 50, 60, 70, 80, 90, or 95 percent of incident ultraviolet radiation in a wavelength range from greater than 230 nanometers, greater than 235 nm, or greater than 240 nm, to 400 nanometers. At least 50, 60, 70, 80, 90, or 95 percent of the ultraviolet radiation having a wavelength between at least 230 nanometers and 400 nanometers transmitted through the ultraviolet mirror is absorbed by the ultraviolet mirror film.

For the particular embodiment shown in FIG. 11, the housing 1102 is formed in the shape of a parabolic collimator to cause the directions of motion of the emitted UV-C radiation 1014 to become more aligned in a specific direction (i.e., to produce collimated light having parallel rays). Suitable parabolic collimators are known to those skilled in the art, and include, for example, those described in U.S. Pat. No. 8,921,813 B2.

Light collimators can be designed to collimate light from a point source can be collimated (focused) using a parabolic (elliptical) reflective optical element. The main requirements are that the source be located near the focal point of the optical element and that the source be relatively small compared with the size of the optical element. Light concentrators can be designed utilizing a surface of revolution generated from a section of an ellipse with the source at one focus and the target at the other focus of the ellipse. The source at one focus shines toward the closest vertex of the ellipse. The section of the ellipse used to generate the surface of revolution is the section defined by the latus rectum at the source and the closest vertex to the source. The latus rectum must be larger than the source so that the concentrator can collect most of the light from the source. If the source and target were points, all the light from the source would be collected at the target.

Light from a point source can be collimated (focused) using a parabolic (elliptical) reflective optical element, and one suitable collimator for the system comprises a parabolic collimator. The main requirements are that the source be located near the focal point of the optical element and that the source be relatively small compared with the size of the optical element. In most applications, the optical element must be designed for practical considerations such as the size of the light source and the allowed amount of space of the optical element. Given a source diameter Ds (width in 1D) and a design volume consisting of a height Hv and diameter Dv (width in 1D), it is possible to derive an equation for the shape of a near-optimum parabolic reflector:

$$y=a*(x+b)^2+\text{offset}$$

where $a=Hv/((Dv/2)^2-(Ds/2)^2)$, $b=-Dv/2$ and $\text{offset}=-a*(Ds/2)^2$;

We further need to select Hv and/or Dv such that the focus of the parabola coincides with the location of the light source at [x=Dv/2, y=0], which is achieved by choosing:

$$Hv=((Dv/2)^2-(Ds/2)^2/Ds$$

The resulting optical element is near optimal given the physical constraints of the system. Following the etendue conservation principle, the amount of collimation is proportional to $(Dv/Ds)^2$, with higher design volumes resulting is greater collimation. The cut-off angle of this optical element is given by:

$$\text{Theta}=+/-\arctan((Dv/2+Ds/2)/Hv)$$

Methods of Using UV-C Disinfection Devices

Figure 12:
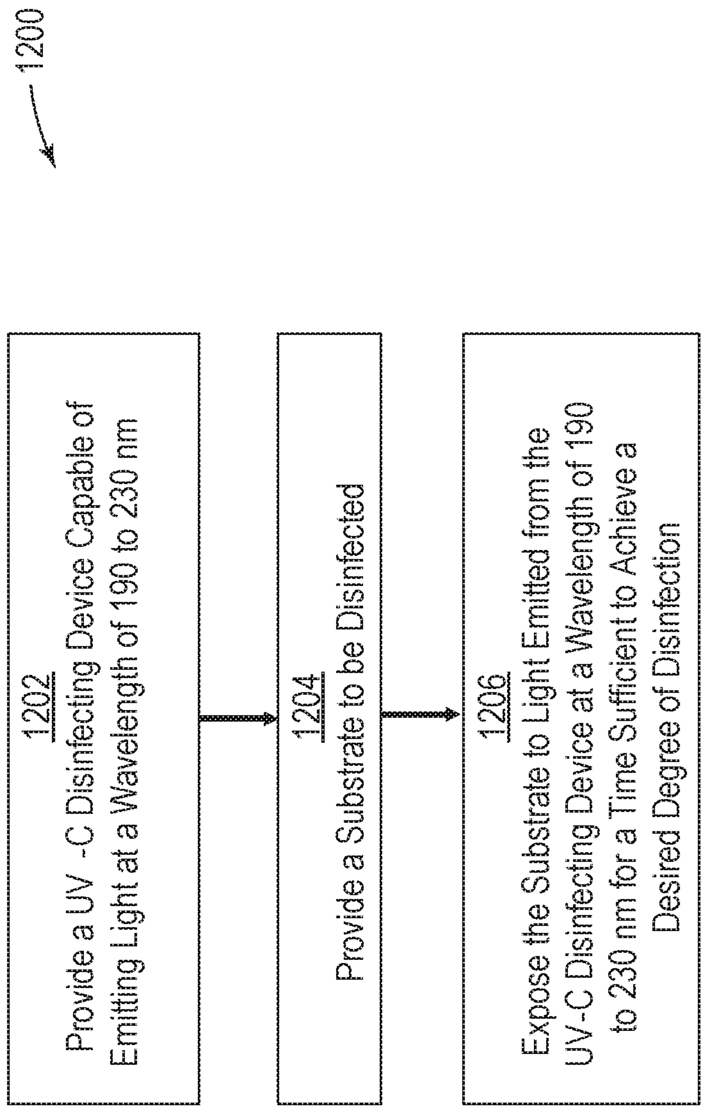
FIG. 12 is a flowchart illustrating an exemplary method of using a UV-C disinfecting device to disinfect a surface.

FIG. 12 is a flowchart illustrating an exemplary method 1200 of using a UV-C disinfecting device to disinfect a material The method 1200 comprises providing the disinfecting device as described in any of the embodiments disclosed herein (1202), directing ultraviolet radiation emitted by the ultraviolet radiation source through the UV-C band pass mirror film (1204) and exposing the at least one material to the ultraviolet radiation passing through the UV-C band pass mirror film for a time sufficient to achieve a desired degree of disinfection of the at least one material (1206).

The ultraviolet radiation passing through the UV-C band-pass mirror film is in a wavelength range from at least 100 nm, 125 nm, 150 nm, 160 nm, 170 nm, 180 nm or 190 nm, to less than 280 nm, 270 nm, 260 nm, 250 nm, 240 nm, or 230 nm, and does not substantially include UV-A and UV-B radiation at a wavelength of from 280 nm to 400 nm. Preferably, the ultraviolet radiation passing through the UV-C band-pass mirror film is in a wavelength range from 190 nm to 230 nm, as shown in FIG. 12.

In some exemplary embodiments, the disinfecting device may be employed in a room where human beings will be present. In certain exemplary embodiments, exposing the at least one material to the ultraviolet radiation passing through the UV-C band-pass mirror film is performed until achievement of a log 2, log 3, log 4, or greater reduction in an amount of at least one microorganism present on or in the at least one material, as compared to an amount of the at least one microorganism present prior to exposing the at least one material to the ultraviolet radiation passing through the UV-C band-pass mirror film.

As used herein, the term "microorganism" refers to any cell or particle having genetic material suitable for analysis or detection (including, for example, bacteria, yeasts, viruses, and bacterial endospores). Log reduction values (LRV) may be determined by measuring the number of colonies of a microorganism present on or in a material prior to disinfection via an exemplary method, disinfecting the material using the method, measuring the number of colonies present on or in the material following disinfection, then calculating the LRV based on colony counts obtained. The method of measuring the number of colony forming units (cfus) on or in a material will vary based on the form of the particular material.

For instance, a solid may be swabbed, and a liquid or gas volumetrically sampled (and concentrated if necessary). The cfus may be measured, for instance, using a culture-based method, an imaging detection method, a fluorescence-based detection method, a colorimetric detection method, an immunological detection method, a genetic detection method, or a bioluminescence-based detection method. The LRV is then calculated using the formula below:

LRV=(Log of cfus/area or volume of pre-disinfected material)−(Log of cfus/area or volume of disinfected material)

Generally, the at least one material comprises at least one of a solid, a liquid, or a gas. When the device is used in the method, the at least one material is typically located within the housing of the device at the time of exposure to UV-C radiation. As discussed above, in some cases, it is preferable to expose the material(s) to ultraviolet radiation having wavelengths of 190 nm or greater, 195 nm, or 200 nm or greater, to 230 nm, 235 nm, or 240 nm.

In certain presently preferred embodiments, during the method the one or more materials is exposed to 10, 8, 6, 5, 4, 3, 2, or 1 percent or less of ultraviolet radiation having a wavelength of greater than 230 nanometers, 235 nm, or 240 nm, to 400 nanometers that is emitted by the broadband UV-C source. This is accomplished by effective absorption of those wavelengths by the absorbent layer and/or a housing, such that 90 percent or more of ultraviolet radiation having a wavelength of greater than 230 nanometers, 235 nm, or 240 nm, to 400 nanometers is absorbed instead of directed at and/or reflected towards the material(s) during the method.

Components of the UV-C Emitting Disinfecting Device

Housing

The material(s) of which the housing 902 is comprised are not particularly limited, and may include for instance metal, plastic, ceramic (including glass), concrete, or wood. In certain embodiments, the housing 902 is formed of a heat-resistant or heat-transfer material that can withstand heat generated by absorption of certain wavelengths of light from the broadband UV-C radiation source disposed within the housing 902.

Preferably, any (co)polymeric material used in the housing 902 that is directly exposed to emission of light from the broadband UV-C radiation source 904 is located at least 3 centimeters (cm), 3.25 cm, 3.5 cm, 3.75 cm, or at least 4 cm away from the broadband UV-C radiation source 904 to minimize damage from exposure to the exposure to wavelengths of light that have not been reflected by the optional ultraviolet mirror film 906.

Typically, in disinfecting devices according to the present disclosure, the broadband UV-C radiation source 904 is configured to direct light at the optional ultraviolet mirror film 906. This allows the ultraviolet mirror film 906 to reflect back wavelengths of light in the desirable range (e.g., 190 nm to 240 nm) while transmitting to the UV light impermeable housing 902 and/or absorbing wavelengths of light greater than the maximum of the range (e.g., greater than 240 nm).

Broadband UV-C Radiation Sources

Suitable broadband UV-C radiation sources for use include any of a low pressure mercury lamp, a medium pressure mercury lamp, a xenon arc lamp, or an excimer lamp. Suitable low pressure mercury lamps include those commercially available from Heraeus-Noblelight (Hanau, Germany), including low pressure mercury amalgam lamps.

For instance, a low pressure mercury lamp can provide a peak emission at approximately 254 nm and minimal emission at wavelengths about 245 nm and below as well as about 260 nm and above. Suitable medium pressure mercury lamps include those commercially available from Helios Quartz Americas (Sylvania, OH). Employing a Type 214 quartz sleeve or a synthetic quartz sleeve with a medium pressure mercury lamp can increase the amount of emission at 200 nm to 51% or 89%, respectively.

Although the peak emission of medium pressure mercury lamps is at approximately 320 nm, medium pressure mercury lamps are polychromatic and also have several significant emission peaks between about 245 nm and about 300 nm, for instance at approximately 265 nm, as well as a broad emission band between about 210 nm and about 240 nm.

Suitable xenon arc lamps are commercially available from Atlas Material Testing Technology, Inc., (Chicago, IL), Newport (Irvine, CA), and Xenex (San Antonio, TX) Xenon arc lamps tend to have broad emission spectra starting somewhere between about 200 nm and 250 nm, and extending beyond 800 nm, with some minor peaks at about 475 nm and about 775 nm.

Examples of excimer ultraviolet radiation sources include lamps such as those commercially available from Osram (Massachusetts, United States), Heraeus-Noblelight (Hanau, Germany), Ushio (Tokyo, Japan), and those described in Kogelschatz, Applied Surface Science, 54 (1992), 410-423, glow discharge lamps such as those described in EP Patent Appl. 521,553 (assigned to N. V. Philips), deuterium lamps available from Hamamatsu (Hamamatsu City, Japan), microwave driven lamps such as those described in Kitamura et al, Applied Surface Science, 79/80 (1994), 507-513 and DE 4302555 A1 (assigned to Fusion Systems), and excimer lamps pumped by a volume discharge with ultraviolet preionization as described in Tech. Phys, 39(10), 1054 (1994). Excimer ultraviolet radiation sources often comprise krypton bromide or krypton chloride. For instance, a deuterium lamp typically has emission spectra showing a broad peak bandwidth between about 200 nm and about 280 nm, then tailing off between about 280 nm to about 700 nm.

The ultraviolet mirror and the absorbent layer are according to any of the embodiments of these portions of the multilayer article of the first aspect, described in detail above. The broadband UV-C radiation source is according to any of the embodiments of the broadband UV-C radiation source of the second aspect, described in detail above.

UV-C Mirror Films

The disinfection device according to the present disclosure may include as components one or more UV-C mirror films which can serve as either UV-C band-pass filter mirror films capable of selectively passing UV-C radiation, or UV-C (and optionally UV-A and UV-B) reflecting protective mirror films.

Band-Pass Filter UV-C Mirror Films

In some embodiments of multilayer optical films described herein, the at least first optical layer comprises inorganic material (e.g., at least one of zirconium oxynitride, hafnia, alumina, magnesium oxide, yttrium oxide, lanthanum fluoride, or neodymium fluoride), and wherein the second optical layer comprises inorganic material (e.g., at least one of silica, aluminum fluoride, magnesium fluoride, calcium fluoride, silica alumina oxide or alumina doped silica). Exemplary materials are available, for example, from Materion Corporation (Mayfield Heights, OH), and Umicore Corporation (Brussels, Belgium).

In any of the foregoing embodiments, incident visible light transmission through at least the plurality of alternating first and second optical layers is greater than 30 percent over at least a 30-nanometer wavelength reflection bandwidth in a wavelength range from at least 400 nanometers to 750 nanometers.

In any of the foregoing embodiments, the at least first optical layer comprises at least one of titania, zirconia, zirconium oxynitride, hafnia, or alumina, and wherein the second optical layer comprises at least one of silica, aluminum fluoride, or magnesium fluoride.

Ultraviolet Radiation Reflecting Mirror Films

The present disclosure also describes multilayer ultraviolet radiation reflecting mirror films which can be used within the UV radiation impermeable housing of a disinfecting device to reflect UV radiation from the broadband UV light source to a window in the disinfecting device covered with the multilayer UV-C mirror film acting as a band-pass filter to allow emission of a substantial amount of the UV-C radiation useful in disinfection of surfaces.

In some particularly advantageous embodiments, the device further includes an ultraviolet mirror film positioned within the housing so as to reflect ultraviolet radiation emitted by the ultraviolet radiation source. The ultraviolet mirror film includes a multiplicity of alternating first and second optical layers collectively reflecting at least 50, 60, 70, 80, 90, or 95 percent of incident UV-C ultraviolet radiation in a wavelength range from at least 100 nm, 125 nm, 150 nm, 160 nm, 170 nm, 180 nm, 190 nm, or 200 nm, to 400 nm, 300 nm, 280 nm, 270 nm, 260 nm, 250 nm, 240 nm or 230 nm, and collectively transmitting at least 50, 60, 70, 80, 90, or 95 percent of incident ultraviolet radiation in a wavelength range from greater than 230 nanometers, greater than 235 nm, or greater than 240 nm, to 400 nanometers. At least 50, 60, 70, 80, 90, or 95 percent of the ultraviolet radiation having a wavelength between at least 230 nanometers and 400 nanometers transmitted through the ultraviolet mirror is absorbed by the ultraviolet mirror film.

UV-C (and Optionally UV-A and UV-B) Reflecting Protective Films

Furthermore, because some surfaces (e.g., (co)polymeric surfaces) being disinfected with ultraviolet radiation may need protection from even UV-C ultra-violet light, the present disclosure also relates to UV-C mirror protection films which can reflect UV-C radiation and optionally one or more of UV-A and UV-B radiation, thereby protecting an underlying surface to which the UV mirror protection film has been applied from damage due to the effects of UV irradiation exposure.

Thus, in another aspect, the present disclosure describes UV-C mirror films including a substrate comprised of a fluoropolymer; a multilayer optical film disposed on a major surface of the substrate, wherein the multilayer optical film is comprised of at least a plurality of alternating first and second optical layers collectively reflecting at an incident light angle of at least one of 0°, 30°, 45°, 60°, or 75°, at least 30 percent of incident ultraviolet radiation over at least a 30-nanometer wavelength reflection bandwidth in a wavelength range from at least 100 nanometers to 280 nanometers or optionally in a wavelength range from at least 240 nm to 400 nm; and a heat-sealable adhesive layer disposed on a major surface of the multilayer optical film opposite the substrate.

In one exemplary embodiment, the present disclosure describes UV-C reflecting mirror films comprising a substrate comprised of a fluoropolymer; a multilayer optical film disposed on a major surface of the substrate, wherein the multilayer optical film is comprised of at least a plurality of alternating first and second optical layers collectively reflecting at an incident light angle of at least one of 0°, 30°, 45°, 60°, or 75°, at least 30 percent of incident ultraviolet radiation over at least a 30-nanometer wavelength reflection bandwidth in a wavelength range from at least 100 nanometers to 280 nanometers; and a heat-sealable adhesive layer disposed on a major surface of the multilayer optical film opposite the substrate.

Referring now to FIG. 1, exemplary UV-C mirror film 10 comprising a fluoropolymer substrate 11, a multilayer optical film 20 (e.g., a UV-C mirror film) disposed on a major surface of the substrate, and an optional adhesive layer 14 disposed on a major surface of the multilayer optical film 20 opposite the substrate 11. The multilayer optical film 20 is comprised of first optical layers 12A, 12B, 12N and second optical layers 13A, 13B, 13N. In some exemplary embodiments, an optional protective film 15, preferably comprised of a fluoropolymer (co)polymer, is disposed on a major surface of the heat-sealable adhesive layer 14 opposite the multilayer optical film 20.

When used as a band-pass filter, the UV-C mirror film construction is preferably a multilayer dielectric mirror that comprises at least nine alternating layers of inorganic HIO and inorganic LIO or at least 100 layers of fluoropolymer (PVDF or ETFE) HIO and fluoropolymer (THV or FEP) LIO. The UV-C transparent fluoropolymer substrate 11 can either be positioned above the multilayer optical film 20 as shown in FIG. 1, or below the multilayer optical film 20 (not shown). If the UV-C transparent fluoropolymer substrate 11 is positioned below the multilayer optical film 20, the optional adhesive layer may be positioned adjacent to the multilayer optical film 20 opposite the fluoropolymer substrate 11, or may be positioned adjacent to the fluoropolymer substrate opposite the multilayer optical film 20.

In some such embodiments, the optional adhesive layer can be coated onto or coextruded with a fluoropolymer (co)polymer, preferably having a melting point greater than 150° C., to protect adhesives such as polyolefin copolymers that are less UV-C stable, but which are lighter and less expensive. Silicone adhesives are also contemplated as a useful embodiment of this invention.

Fluoropolymer Substrates

In any of the foregoing embodiments, the fluoropolymer substrate is comprised of a (co)polymer comprising tetrafluoroethylene, hexafluoropropylene, vinylidene fluoride, a perfluoroalkoxy alkane, or a combination thereof. Suitable fluoropolymer substrates are available under the trade name "NOWOFLON" from Nowofol Kunststoffprodukte GmbH KG (Siegsdorf, Germany), of which NOWOFLON THV815 is currently preferred.

Multilayer Optical Films

In general, multilayer optical films described herein comprise at least 3 layers (typically in a range from 3 to 2000 total layers or more). Multilayer optical films described herein comprise at least a plurality of alternating first and second optical layers collectively reflecting at an incident light angle of at least one of 0°, 30°, 45°, 60°, or 75°, at least 30 (in some embodiments, at least 40, 45, 50, 55, 60, 65, 70, 75, 80, 85, or even at least 90) percent of incident ultraviolet (UV) light (i.e., any light having a wavelength in a range from 100 to less than 400 nm) over at least a 30-nanometer wavelength reflection bandwidth in a wavelength range from at least 100 to 280 (in some embodiments, at least 180 to 280, or even at least 200 to 280) nm. In some embodiments, the multilayer optical film has a UV reflectivity (Reflectance) greater than 90% (in some embodiments, greater than 99%), at least one of 222 nm, 254 nm, 265 nm, or 275 nm.

In some embodiments, multilayer optical films described herein have a UV transmission band edge in a range from 10 to 90 percent transmission spanning less than 20 (in some embodiments, less than 15, or even less than 10) nanometers.

Optical Layers

In any of the foregoing embodiments, the at least first optical layer comprises at least one polyethylene (co)polymer, and wherein the second optical layer comprises at least one fluoropolymer selected from a tetrafluoroethylene (co) polymer, a hexafluoropropylene (co)polymer, a vinylidene fluoride (co)polymer, a hexafluoropropylene (co)polymer, a perfluoroalkoxy alkane (co)polymer, or a combination thereof. In some such embodiments, the at least one fluoropolymer is crosslinked.

In some embodiments of multilayer optical films described herein, the at least first optical layer 12A comprises polymeric material (e.g., at least one of polyvinylidene fluoride (PVDF), ethylene tetrafluoroethylene (ETFE)), and wherein the second optical layer 13A comprises polymeric material (e.g., at least one of a copolymer (THV) or a polyethylene copolymer comprising subunits derived from tetrafluoroethylene (TFE), hexafluoropropylene (HFP), and vinylidene fluoride (VDF), a copolymer (FEP) comprising subunits derived from tetrafluoro-ethylene (TFE) and hexafluoropropylene (HFP), or perfluoroalkoxy alkane (PFA)).

Exemplary materials for making the optical layers that reflect blue light (e.g., the first and second optical layers) include polymers (e.g., polyesters, (co)polyesters, and modified (co)polyesters). In this context, the term "polymer" will be understood to include homopolymers and copolymers, as well as polymers or copolymers that may be formed in a miscible blend, for example, by co-extrusion or by reaction, including transesterification. The terms "polymer" and "copolymer" include both random and block copolymers.

Polyesters suitable for use in some exemplary multilayer optical films constructed according to the present disclosure generally include dicarboxylate ester and glycol subunits and can be generated by reactions of carboxylate monomer molecules with glycol monomer molecules. Each dicarboxylate ester monomer molecule has two or more carboxylic acid or ester functional groups and each glycol monomer molecule has at least two hydroxy functional groups. The dicarboxylate ester monomer molecules may all be the same or there may be two or more different types of molecules. The same applies to the glycol monomer molecules. Also included within the term "polyester" are polycarbonates derived from the reaction of glycol monomer molecules with esters of carbonic acid.

Examples of suitable dicarboxylic acid monomer molecules for use in forming the carboxylate subunits of the polyester layers include 2,6-naphthalene dicarboxylic acid and isomers thereof; terephthalic acid; isophthalic acid; phthalic acid; azelaic acid; adipic acid; sebacic acid; norbornenedicarboxylic acid; bi-cyclo-octane dicarboxylic acid; 1,4-cyclohexanedicarboxylic acid and isomers thereof; t-butylisophthalic acid, trimellitic acid, sodium sulfonated isophthalic acid; 4,4'-biphenyl dicarboxylic acid and isomers thereof; and lower alkyl esters of these acids, such as methyl or ethyl esters. The term "lower alkyl" refers, in this context, to $C_1$-$C_{10}$ straight-chain or branched alkyl groups.

Examples of suitable glycol monomer molecules for use in forming glycol subunits of the polyester layers include ethylene glycol; propylene glycol; 1,4-butanediol and isomers thereof; 1,6-hexanediol; neopentyl glycol; polyethylene glycol; diethylene glycol; tricyclodecanediol; 1,4-cyclohexanedimethanol and isomers thereof; norbornanediol; bicyclooctanediol; trimethylolpropane; pentaerythritol; 1,4-benzenedimethanol and isomers thereof; Bisphenol A; 1,8-dihydroxybiphenyl and isomers thereof; and 1,3-bis(2-hydroxyethoxy)benzene.

Another exemplary birefringent polymer useful for the reflective layer(s) is polyethylene terephthalate (PET), which can be made, for example, by reaction of terephthalic dicarboxylic acid with ethylene glycol. Its refractive index for polarized incident light of 550 nm wavelength increases when the plane of polarization is parallel to the stretch direction from about 1.57 to as high as about 1.69. Increasing molecular orientation increases the birefringence of PET. The molecular orientation may be increased by stretching the material to greater stretch ratios and holding other stretching conditions fixed. Copolymers of PET (CoPET), such as those described in U.S. Pat. No. 6,744,561 (Condo et al.) and U.S. Pat. No. 6,449,093 (Hebrink et al.), the disclosures of which are incorporated herein by reference, are particularly useful for their relatively low temperature (typically less than 250° C.) processing capability making them more coextrusion compatible with less thermally stable second polymers. Other semicrystalline polyesters suitable as birefringent polymers include polybutylene terephthalate (PBT), and copolymers thereof such as those described in U.S. Pat. No. 6,449,093 (Hebrink et al.) and U.S. Pat. Pub. No. 2006/0084780 (Hebrink et al.), the disclosures of which are incorporated herein by reference. Another useful birefringent polymer is syndiotactic polystyrene (sPS).

First optical layers can also be isotropic high refractive index layers comprising at least one of poly(methyl methacrylate), copolymers of polypropylene; copolymers of polyethylene, cyclic olefin copolymers, cyclic olefin block copolymers, polyurethanes, polystyrenes, isotactic polystyrene, atactic polystyrene, copolymers of polystyrene (e.g., copolymers of styrene and acrylate), polycarbonates, copolymers of polycarbonates, miscible blends of polycarbonates and (co)polyesters, or miscible blends of poly(methyl methacrylate) or poly(vinylidene fluoride.

Second optical layers can also comprise fluorinated copolymers materials such as at least one of fluorinated ethylene propylene copolymer (FEP); copolymers of tetrafluorethylene, hexafluoropropylene, and vinylidene fluoride (THV); copolymers of tetrafluoroethylene, hexafluoropropylene, or ethylene. Particularly useful are melt processible copolymers of tetrafluoroethylene and at least two, or even at least three, additional different comonomers.

Exemplary melt processible copolymers of tetrafluoroethylene and other monomers discussed above include those available as copolymers of tetrafluoroethylene, hexafluoropropylene, and vinylidene fluoride under the trade designations "DYNEON THV 221," "DYNEON THV 230," "DYNEON THV 2030," "DYNEON THV 340GZ", "DYNEON THV 500," "DYNEON THV 610," and "DYNEON THV 815" from Dyneon LLC (Oakdale, MN); "NEOFLON EFEP" from Daikin Industries, Ltd. (Osaka, Japan); "AFLAS" from Asahi Glass Co., Ltd. (Tokyo, Japan); and copolymers of ethylene and tetrafluoroethylene available under the trade designations "DYNEON ET 6210A" and "DYNEON ET 6235" from Dyneon LLC (Oakdale, MN); "TEFZEL ETFE" from E.I. duPont de Nemours and Co. (Wilmington, DE); and "FLUON ETFE" by Asahi Glass Co., Ltd (Tokyo, Japan).

In addition, the second polymer can be formed from homopolymers and copolymers of polyesters, polycarbonates, fluoropolymers, polyacrylates, and polydimethylsiloxanes, and blends thereof.

Other exemplary polymers, for the optical layers, especially for use in the second layer, include homopolymers of polymethylmethacrylate (PMMA), such as those available, for example, from Ineos Acrylics, Inc. (Wilmington, DE) under the trade designations "CP71" and "CP80;" and polyethyl methacrylate (PEMA), which has a lower glass transition temperature than PMMA. Additional useful polymers include copolymers of PMMA (CoPMMA), such as a CoPMMA made from 75 wt. % methylmethacrylate (MMA) monomers and 25 wt. % ethyl acrylate (EA) monomers, (available, for example, from Ineos Acrylics, Inc. (London, England) under the trade designation "PERSPEX CP63" or Arkema Corp., (Philadelphia, PA) under the trade designation "ATOGLAS 510"), a CoPMMA formed with MMA comonomer units and n-butyl methacrylate (nBMA) comonomer units, or a blend of PMMA and poly(vinylidene fluoride) (PVDF).

Additional suitable polymers for the optical layers include polyolefin copolymers such as poly (ethylene-co-octene) (PE-PO) available, for example, under the trade designation "ENGAGE 8200" from Dow Elastomers, Inc. (Midland, MI) and polyethylene methyl acrylate also available, for example, under the trade designation "ELVALOY 1125" from Dow Elastomers, Inc. (Midland, MI); poly (propylene-co-ethylene) (PPPE) available, for example, under the trade designation "Z9470" from Atofina Petrochemicals, Inc. (Houston, TX); and a copolymer of atactic polypropylene (aPP) and isotatctic polypropylene (iPP). The multilayer optical films can also include in the second layers, a functionalized polyolefin (e.g., linear low-density polyethylene-graft-maleic anhydride (LLDPE-g-MA) such as that available, for example, under the trade designation "BYNEL 4105" from E.I. duPont de Nemours & Co., Inc. Wilmington, DE).

The selection of the polymer combinations used in creating the multilayer optical film depends, for example, upon the desired bandwidth that will be reflected. Higher refractive index differences between the first optical layer polymer and the second optical layer polymer create more optical power thus enabling more reflective bandwidth. Alternatively, additional layers may be employed to provide more optical power. Exemplary combinations of birefringent layers and second polymer layers may include, for example, the following: PET/THV, PET/SPDX, PET/CoPMMA, CoPEN/PMMA, CoPEN/SPDX, sPS/SPDX, sPS/THV, CoPEN/THV, PET/blend of PVDF/PMMA, PET/fluoropolymers, sPS/fluoroelastomers, and CoPEN/fluoropolymers.

Exemplary material combinations for making the optical layers that reflect UV light (e.g., the first and second optical layers) include poly(methyl methacrylate) (PMMA) (e.g., first optical layers)/THV (e.g., second optical layers), PMMA (e.g., first optical layers)/blend of PVDF/PMMA (e.g., second optical layers), PC (polycarbonate) (e.g., first optical layers)/PMMA (e.g., second optical layers), PC(polycarbonate) (e.g., first optical layers)/blend of PMMA/PVDF (e.g., second optical layers), copolyethylene (e.g., polyethylene methyl acrylate) (e.g., first optical layers)/THV (e.g., second optical layers), blend of PMMA/PVDF (e.g., first optical layers)/blend of PVDF/PMMA (e.g., second optical layers) and PET (e.g., first optical layers)/CoPMMA (e.g., second optical layers).

In some embodiments, the first optical layer is a fluoropolymer and the second optical layer is a fluoropolymer. Examples of the materials that are desirable for such embodiments include ETFE/THV, PMMA/THV, PVDF/FEP, ETFE/FEP, PVDF/PFA, and ETFE/PFA. In one exemplary embodiment, THV available, for example, under the trade designation "DYNEON THV 221 GRADE" or "DYNEON THV 2030 GRADE" or "DYNEON THV 815 GRADE" from Dyneon LLC (Oakdale, MN), are employed as the second optical layer with PMMA as the first optical layer for multilayer UV-C reflecting mirrors reflecting 300-400 nm. In another exemplary embodiment, THV, available, for example, under the trade designation "DYNEON THV 221 GRADE" or "DYNEON THV 2030 GRADE" or "DYNEON THV 815 GRADE" from Dyneon LLC (Oakdale, MN) are employed as the second optical layer, preferably in combination with "ELVALOY 1125" available from Dow Elastomers, Inc. (Midland, MI) as the first optical layer.

Exemplary material for making the optical layers that absorb UV light, or blue light, include COC, EVA, TPU, PC, PMMA, CoPMMA, siloxane polymers, fluoropolymers, THV, PET, PVDF or blends of PMMA and PVDF.

A UV absorbing layer (e.g., a UV protective layer) aids in protecting the visible/IR-reflective optical layer stack from UV-light caused damage/degradation over time by absorbing UV-light (e.g., any UV-light) that may pass through the UV-reflective optical layer stack. In general, the UV-absorbing layer(s) may include any polymeric composition (i.e., polymer plus additives), including pressure-sensitive adhesive compositions, that is capable of withstanding UV-light for an extended period of time.

LED UV light, in particular the ultraviolet radiation from 280 to 400 nm, can induce degradation of plastics, which in turn results in color change and deterioration of optical and mechanical properties. Inhibition of photo-oxidative degradation is important for outdoor applications wherein long-term durability is mandatory. The absorption of UV-light by polyethylene terephthalates, for example, starts at around 360 nm, increases markedly below 320 nm, and is very pronounced at below 300 nm. Polyethylene naphthalates strongly absorb UV-light in the 310 to 370 nm range, with an absorption tail extending to about 410 nm, and with absorption maxima occurring at 352 nm and 337 nm. Chain cleavage occurs in the presence of oxygen, and the predominant photooxidation products are carbon monoxide, carbon dioxide, and carboxylic acids. Besides the direct photolysis of the ester groups, consideration has to be given to oxidation reactions, which likewise form carbon dioxide via peroxide radicals.

A UV absorbing layer may protect the multilayer optical film by reflecting UV light, absorbing UV light, scattering UV light, or a combination thereof. In general, a UV absorbing layer may include any polymer composition that is capable of withstanding UV radiation for an extended period of time while either reflecting, scattering, or absorbing UV radiation. Examples of such polymers include PMMA, CoPMMA, silicone thermoplastics, fluoropolymers, and their copolymers, and blends thereof. An exemplary UV absorbing layer comprises PMMA/PVDF blends.

Optional Adhesive Layers

In any of the foregoing embodiments, the optional adhesive layer comprises a (co)polymer. In any of the foregoing embodiments, the (co)polymer is selected from an olefinic (co)polymer, a (meth)acrylate (co)polymer, a urethane (co) polymer, a fluoropolymer, a silicone (co)polymer, or a combination thereof. In certain such embodiments, the (co) polymer is an olefinic (co)polymer selected from low density polyethylene, linear low density polyethylene, ethylene vinyl acetate, polyethylene methyl acrylate, polyethylene octene, polyethylene propylene, polyethylene butene, polyethylene maleic anhydride, polymethyl pentene, polyisobutene, polyisobutylene, polyethylene propylene diene, cyclic olefin copolymers, and blends thereof.

In some of the foregoing embodiments, the (co)polymer has a melting temperature less than 160° C. In certain such embodiments, the (co)polymer is crosslinked. In some such embodiments, the (co)polymer further comprises an ultraviolet radiation absorber, a hindered amine light stabilizer, an anti-oxidant, or a combination thereof. In further such embodiments, the ultraviolet radiation absorber is selected from a benzotriazole compound, a benzophenone compound, a triazine compound, or a combination thereof.

One exemplary heat sealable fluoropolymer adhesive material is available from Dyneon LLC (Oakdale, MN) as THV221GZ. Another exemplary heat sealable fluoropolymer adhesive material is available from 3M Dyneon LLC (Oakdale, MN) as THV340GZ. Other exemplary heat sealable adhesives for photovoltaic modules can also be found in patent applications WO2013066459A1 (Rasal et. al.) and WO2013066460A1 (Rasal et. al.), the entire disclosures of which are incorporated herein by reference.

The optional adhesive layer can be cross-linked with photo initiators or thermal initiators During or after lamination to a photovoltaic cell. Exemplary photo initiators include benzophones, ortho-methoxy benzophone, para-ethoxy benzophenone, acetophenones, ortho-methoxy-acetophenone, hexaphenones, polymethylvinyl ketone, polyvinylaryl ketones, oligo (2-hydroxy-2-methyl-1-4(1-methylvinyl) propanone, and 2-hydroxy-2-methyl-1-phenyl propan-1-one such as Escacure KIP150 available from Arkema Sartomer Exton, PA). The heat sealable adhesive layer may be cured with cross-linking through radiation such as using X-ray irradiation, gamma radiation, ultraviolet electromagnetic radiation, and electron beam irradiation.

Cross-linking may also be facilitated with thermal chemical cross-linking agents including; peroxides, amines, silanes, and sulfur containing compounds. Exemplary organic peroxide cross-linking agents include 2,7-dimethyl-2,7-di(t-butylperoxy) octadiyne-3,5 and 2,7-dimethyl-2,7-di (peroxy ethyl carbonate) octadiyne-3,5. Another exemplary cross-linking agent is dicumyl peroxide available from Elf Atochem North America (St. Louis, MO) as Luperox 500R.

Optional Additives

Exemplary adhesive layers may include UV absorbers, hindered amine light stabilizers, and anti-oxidants. Benzotriazole, benzophenone, and triazine UV absorbers are available from BASF U.S.A. (Florham Park, NJ) under the tradenames Tinuvin and Chemisorb such as Tinuvin P, Tinuvin 326, Tinuvin 327, Tinuvin 360, Tinuvin 477, Tinuvin 479, Tinuvin 1577, and Tinuvin 1600. Suitable hindered amine light stabilizers are also available from BASF as Tinuvin 123, Tinuvin 144, and Tinuvin 292.

Exemplary anti-oxidants are also available from BASF (Florham Park, NJ) under the tradenames Irganox, Irgafos, and Irgastab. Exemplary antioxidants for polyolefins include Irganox 1010, Irganox 1076, and Irgafos 168. Additional olefin polymer stabilizers are available from Solvay under the tradenames CYTEC, CYASORB, CYANOX and CYNERGY such as CYASORB THT460, CYASORB UV3529, CYNERGY 400, and CYANOX 2777.

A variety of optional additives may be incorporated into an optical layer to make it UV absorbing. Examples of such additives include at least one of an ultraviolet absorber(s), a hindered amine light stabilizer(s), or an anti-oxidant(s).

Particularly desirable UV absorbers are red shifted UV absorbers (RUV-A) which absorb at least 70% (in some embodiments, at least 80%, or even greater than 90%) of the UV light in the wavelength region from 180 nm to 400 nm. Typically, it is desirable if the RUV-A is highly soluble in polymers, highly absorptive, photo-permanent and thermally stable in the temperature range from 200° C. to 300° C. for extrusion process to form the protective layer. The RUV-A can also be highly suitable if they can be copolymerizable with monomers to form protective coating layer by UV curing, gamma ray curing, e-beam curing, or thermal curing processes.

RUV-As typically have enhanced spectral coverage in the long-wave UV region, enabling it to block the high wavelength UV light that can cause yellowing in polyesters. Typical UV protective layers have thicknesses in a range from 13 micrometers to 380 micrometers (0.5 mil to 15 mils) with a RUV-A loading level of 2-10 wt. %. One of the most effective RUV-A is a benzotriazole compound, 5-trifluoromethyl-2-(2-hydroxy-3-alpha-cumyl-5-tert-octylphenyl)-2H-benzotriazole (available under the trade designation "CGL-0139" from BASF (Florham Park, NJ).

Other exemplary benzotriazoles include 2-(2-hydroxy-3,5-di-alpha-cumylphehyl)-2H-benzotriazole, 5-chloro-2-(2-hydroxy-3-tert-butyl-5-methylphenyl)-2H-benzotiazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-alpha-cumyl-5-tert-octylphenyl)-2H-benzotriazole, 2-(3-tert-butyl-2-hydroxy-5-methylphenyl)-5-chloro-2H-benzotriazole. Further exemplary RUV-As includes 2(-4,6-diphenyl-1-3,5-triazin-2-yl)-5-hexyloxy-phenol.

Other exemplary UV absorbers include those available from BASF (Florham Park, NJ) under the trade designations "TINUVIN 1577," "TINUVIN 900," "TINUVIN 1600," and "TINUVIN 777." Additional exemplary UV absorbers are available, for example, in a polyester master batch under the trade designation "TA07-07 MB" from Sukano Polymers Corporation (Dunkin, SC).

An exemplary UV absorber for polymethylmethacrylate is a masterbatch available, for example, under the trade designation "TA11-10 MBO1" from Sukano Polymers Corporation (Dunkin, SC).

An exemplary UV absorber for polycarbonate is a masterbatch from Sukano Polymers Corporation, under the trade designations "TA28-09 MB01." In addition, the UV absorbers can be used in combination with hindered amine light stabilizers (HALS) and anti-oxidants. Exemplary HALS include those available from BASF, under the trade designation "CHIMASSORB 944" and "TINUVIN 123." Exemplary anti-oxidants include those obtained under the trade designations "IRGANOX 1010" and "ULTRANOX 626", also available from BASF (Florham Park, NJ).

Other additives may be included in a UV absorbing layer (e.g., a UV protective layer). Small particle non-pigmentary zinc oxide and titanium oxide can also be used as blocking or scattering additives in a UV absorbing layer. For example, nano-scale particles can be dispersed in polymer or coating substrates to minimize UV radiation degradation. The nano-scale particles are transparent to visible light while either scattering or absorbing harmful UV radiation thereby reducing damage to thermoplastics.

U.S. Pat. No. 5,504,134 (Palmer et al.), the entire disclosure of which is incorporated herein by reference, describes attenuation of polymer substrate degradation due to ultraviolet radiation through the use of metal oxide particles in a size range of about 0.001 to about 0.2 micrometer (in some embodiments, about 0.01 micrometer to about 0.15) micrometer in diameter.

U.S. Pat. No. 5,876,688 (Laundon), the entire disclosure of which is incorporated herein by reference, describes a method for producing micronized zinc oxide that are small enough to be transparent when incorporated as UV blocking and/or scattering agents in paints, coatings, finishes, plastic articles, cosmetics and the like which are well suited for use in the present invention. These fine particles such as zinc oxide and titanium oxide with particle size ranged from 10 nm-100 nm that can attenuate UV radiation are available, for example, from Kobo Products, Inc. (South Plainfield, NJ). Flame retardants may also be incorporated as an additive in a UV protective layer.

In addition to adding UV absorbers, HALS, nano-scale particles, flame retardants, antimicrobials, wetting agents, and anti-oxidants to a UV absorbing layer, the UV absorbers, HALS, nano-scale particles, flame retardants, and anti-oxidants can be added to the multilayer optical films, and any optional durable top coat layers.

Fluorescing molecules and optical brighteners can also be added to a UV absorbing layer, the multilayer optical layers, an optional hardcoat layer, or a combination thereof. Blue light absorbing dyes or pigments are available, for example, from Clariant Specialty Chemicals (Charlotte, NC) under the trade designation "PV FAST YELLOW," and can be added to the skin layers or top coat. In an exemplary embodiment, antimicrobial agents, and wetting agents, can be added to the skin layer and they would migrate to the surface exposed to the air. A wetting agent may be necessary to prevent condensation fogging.

The desired thickness of a UV protective layer is typically dependent upon an optical density target at specific wavelengths as calculated by Beers Law. In some embodiments, the UV protective layer has an optical density greater than 3.5, 3.8, or 4 at 380 nm, greater than 1.7 at 390 nm, and greater than 0.5 nm at 400 nm. Those of ordinary skill in the art recognize that the optical densities typically should remain substantially constant over the extended life of the article in order to provide the intended protective function.

The optional UV protective film and any optional additives, may be selected to achieve the desired functions such as UV protection. Those of ordinary skill in the art recognize that there are multiple means for achieving the noted objectives of the UV protective layer. For example, additives that are very soluble in certain polymers may be added to the composition.

Of particular importance, is the permanence of the additives in the polymer. The additives should not degrade or migrate out of the polymer. Additionally, the thickness of the layer may be varied to achieve desired protective results. For example, thicker UV protective layers would enable the same UV absorbance level with lower concentrations of UV absorbers, and would provide more UV absorber permanence attributed to less driving force for UV absorber migration.

One mechanism for detecting the change in physical characteristics is the use of the weathering cycle described in ASTM G155-05a (October 2005) and a D65 light source operated in the reflected mode. Under the noted test, and when the UV protective layer is applied to the article, the article should withstand an exposure of at least 18,700 kJ/$m^2$ at 340 nm before the b* value obtained using the CIE L*a*b* space increases by 5 or less, 4 or less, 3 or less, or 2 or less before the onset of significant cracking, peeling, delamination, or haze.

An exemplary UV-C protective layer is a cross-linked fluoropolymer. The fluoropolymer may be cross-linked with electron beam irradiation. The cross-linked fluoropolymer layer can have a cross-link density gradient with a high cross-link density at its first surface and a lower cross-link at its second surface. Cross-link density gradients can be achieved low electron beam voltages in the range from 50 kV to 150 kV.

Another exemplary UV-C protective layer is a cross-linked silicone polymer. The cross-linked silicone polymer can also comprise nano-silica particles and silsequioxane particles. An exemplary cross-linked silicone polymer coating comprising nano-silica particles is available under the trade designation "GENTOO" from Ulta-Tech International, Inc. (Jacksonville, FL).

Multilayer optical films described herein can be made using general processing techniques, such as those described in U.S. Pat. No. 6,783,349 (Neavin et al.), the entire disclosure of which is incorporated herein by reference.

Exemplary UV-C multilayer optical films and UV-C shielding films described herein are preferably flexible. Flexible UV-C multilayer optical films and UV-C shields can be wrapped around a rod not greater than 1 m (in some embodiments, not greater than 75 cm, 50 cm, 25 cm, 10 cm, 5 cm, or even not greater than 1 cm) in diameter without visibly cracking.

Methods of Making Ultraviolet Band-pass Filter and Reflective [Protective] Mirror Films In further exemplary embodiments, the present disclosure describes a method of making a UV-C mirror film according to any of the preceding UV-C mirror film embodiments. The method includes providing the substrate comprised of the fluoropolymer, providing the multilayer optical film disposed on a major surface of the substrate and heat-sealing the multilayer optical film to the substrate with the heat-sealable adhesive layer. In some presently preferred embodiments, the multilayer optical film is produced using a multilayer co-extrusion die.

Suitable methods for producing a multilayer optical film with a controlled spectrum may include the use of an axial rod heater control of the layer thickness values of coextruded polymer layers as described, for example, in U.S. Pat. No. 6,783,349 (Neavin et al.), the entire disclosure of which is incorporated herein by reference; timely layer thickness profile feedback during production from a layer thickness measurement tool such as an atomic force microscope (AFM), a transmission electron microscope, or a scanning electron microscope; optical modeling to generate the desired layer thickness profile; and repeating axial rod adjustments based on the difference between the measured layer profile and the desired layer profile.

The basic process for layer thickness profile control involves adjustment of axial rod zone power settings based on the difference of the target layer thickness profile and the measured layer profile. The axial rod power increase needed to adjust the layer thickness values in a given feedblock zone may first be calibrated in terms of watts of heat input according to nanometer of resulting thickness change of the layers generated in that heater zone. For example, fine control of the spectrum is possible using 24 axial rod zones for 275 layers. Once calibrated, the necessary power adjustments can be calculated once given a target profile and a measured profile. The procedure is repeated until the two profiles converge.

The layer thickness profile (layer thickness values) of multilayer optical film described herein reflecting at least 50 percent of incident UV light over a specified wavelength range can be adjusted to be approximately a linear profile with the first (thinnest) optical layers adjusted to have about a ¼ wave optical thickness (index times physical thickness) for 100 nm light and progressing to the thickest layers which would be adjusted to be about ¼ wave thick optical thickness for 280 nm light.

Dielectric mirrors, with optical thin film stack designs comprised of alternating thin layers of inorganic dielectric materials with refractive index contrast, are particularly suited for this. In recent decades they are used for applications in UV, Visible, NIR and IR spectral regions. Depending upon the spectral region of interest, there are specific materials suitable for that region. Also, for coating these materials, one of two forms of physical vapor deposition (PVD) are used: evaporation or sputtering. Evaporated coatings rely upon heating the coating material (evaporant) to a temperature at which it evaporates. This is followed by condensation of the vapor upon a substrate. For evaporated dielectric mirror coatings, the electron-beam deposition process is most commonly used.

Sputtered coatings use energetic gas ions to bombard a material ("target") surface, ejecting atoms which then condense on the nearby substrate. Depending upon which coating method is used, and the settings used for that method, thin film coating rate and structure-property relationships will be strongly influenced. Ideally, coating rates should be high enough to allow acceptable process throughput and film performance, characterized as dense, low stress, void free, non-optically absorbing coated layers.

Exemplary embodiments can be designed to have peak reflectance at 254 nm, by both PVD methods. For example, coating discrete substrates by electron-beam deposition method, using $HfO_2$ as the high refractive index material and $SiO_2$ as the low refractive index material. Mirror design has alternating layers of "quarter wave optical thickness" (qwot) of each material, that are coated, layer by layer until, for example, after 13 layers the reflectance at 254 nm is >99%. The bandwidth of this reflection peak is around 80 nm. Quarter wave optical thickness is the design wavelength, here 254 nm, divided by 4, or 63.5 nm. Physical thickness of the high refractive index layers ($HfO_2$) is the quotient of qwot and refractive index of $HfO_2$ at 254 nm (2.41), or 30.00 nm. Physical thickness of the low refractive index layers ($MgF_2$), with 254 nm refractive index at 1.41, is 45.02 nm. Coating a thin film stack, then, which is comprised of alternating layers of $HfO_2$ and $SiO_2$ and designed to have peak reflectance at 254 nm begins by coating layer 1 $HfO_2$ at 30.00 nm.

In electron beam deposition a four-hearth evaporation source is used. Each hearth is cone-shaped and 17 cm 3 volume of $HfO_2$ chunks fill it. The magnetically deflected high voltage electron beam is raster scanned over the material surface as filament current of the beam is steadily, in a pre-programmed fashion, increased.

Upon completion of the pre-programmed step the $HFO_2$ surface is heated to evaporation temperature, about 2500° C., and a source shutter opens, the $HfO_2$ vapor flux emerging from the source in a cosine-shaped distribution and condensing upon the substrate material above the source. For enhancement of coating uniformity, the substrate holders rotate during deposition. Upon reaching the prescribed coating thickness (30.00 nm) the filament current shuts off; the shutter closes and the $HfO_2$ material cools.

For layer 2 the evaporation source is then rotated to a hearth containing chunks of $MgF_2$ and a similar pre-programmed heating process begins. Here, the $MgF_2$ surface temperature is about 950° C. when the source shutter opens and, upon reaching the prescribed coating thickness (45.02 nm), the filament current shuts off; the shutter closes and the $HfO_2$ material cools. This step-wise process is continued, layer by layer, until the total number of design layers is reached. With this optical design, as total layers are increased, from 3 to 13, the resulting peak reflectance increases accordingly, from 40% at 3 layers to >99% at 13 layers.

In another exemplary embodiment, UV transparent films can be coated in continuous roll to roll (R2R) fashion, using ZrON as the high refractive index material and $SiO_2$ as the low refractive index material. The optical design is the same type of thin film stack, alternating qwot layers of the two materials. For ZrON, with refractive index at 254 nm of 2.25, the physical thickness target was 28.22 nm. For $SiO_2$, here sputtered from an aluminum-doped silicon sputter target, with refractive index 1.49, the target thickness was 42.62 nm.

Layer one ZrON is DC sputtered from a pure zirconium sputter target in a gas mixture of argon, oxygen and nitrogen. Whereas argon is the primary sputtering gas, oxygen and nitrogen levels are set to achieve transparency, low absorptance and high refractive index. The film roll transport initially starts at a pre-determined speed, and the sputter source power is ramped to full operating power, followed by introduction of the reactive gases and then achieving steady state condition. Depending upon the length of film to coat, the process continues until total footage is achieved. Here, as the sputter source is orthogonal to and wider than the film which is being coated, the uniformity of coating thickness is quite high.

Upon reaching the desired length of coated film the reactive gases are set to zero and the target is sputtered to a pure Zr surface state. The film direction is next reversed and silicon (aluminum doped) rotary pair of sputter targets has AC frequency (40 kHz) power applied in an argon sputtering atmosphere. Upon reaching steady state, oxygen reactive gas is introduced to provide transparency and low refractive index. At the pre-determined process setting and line speed the second layer is coated over the length which was coated for layer one. Again, as these sputter sources are also orthogonal to and wider than the film being coated, the uniformity of coating thickness is quite high. After reaching the desired length of coated film the reactive oxygen is removed and the target is sputtered in argon to a pure silicon (aluminum doped) surface state. Layers three to five or seven or nine or eleven or thirteen, depending upon peak reflectance target, are coated in this sequence. Upon completion, the film roll is removed for post-processing.

For manufacturing of these inorganic coatings, the electron beam process is best suited for coating discrete parts. Though some chambers have demonstrated R2R film coating, the layer by layer coating sequence would still be necessary. For R2R sputtering of film, it is advantageous to use a sputtering system with multiple sources located around one, or perhaps two, coating drums. Here, for a thirteen layers optical stack design, a two, or even single, machine pass process, with alternating high and low refractive index layers coated sequentially, would be feasible. How many machine passes needed would be contingent upon machine design, cost, practicality of thirteen consecutive sources, and the like. Additionally, coating rates would need to be matched to a single film line speed.

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

EXAMPLES

These examples are offered to further illustrate the various specific and preferred embodiments and techniques. It should be understood, however, that many variations and modifications may be made while remaining within the scope of the present disclosure.

UV-C Service Life Test

UV-C Service Life was determined for certain exemplary UV-C protective mirror films with an enclosure made of aluminum having a 118V RRD-30-8S germicidal fixture manufactured by Atlantic Ultraviolet Corporation, Hauppauge, NY. The fixture contains eight high output instant start 254 nm UV-C lamps. Compressed air was run across the length of the lamps at a pressure of 124 kPa (18 psi) to maintain a constant temperature and minimize temperature-induced loss of lamp output intensity. Test samples were mounted onto aluminum slides containing a window of appropriate size to conduct absorbance measurements using a spectrophotometer) (obtained under the trade designation "SHIMADZU 2550 UV-VIS" from Shimadzu Instruments (Kyoto, Japan).

Continuous light exposures were conducted for discrete time intervals, with removal for absorbance measurement every 100 hours, and placed back into the exposure housing. Samples were placed within the test chamber at a controlled height from and distance along the lamps throughout the duration of experiments. A UV radiometer (obtained under the trade designation "UVPAD" from OPSYTECH Corporation (Makati City, Philippines) was placed within the chamber in line with test samples to gather UV (and specifically UV-C) irradiance and dosage data every 100 hours throughout the exposure process.

Comparative Example 1

Figure 2A:
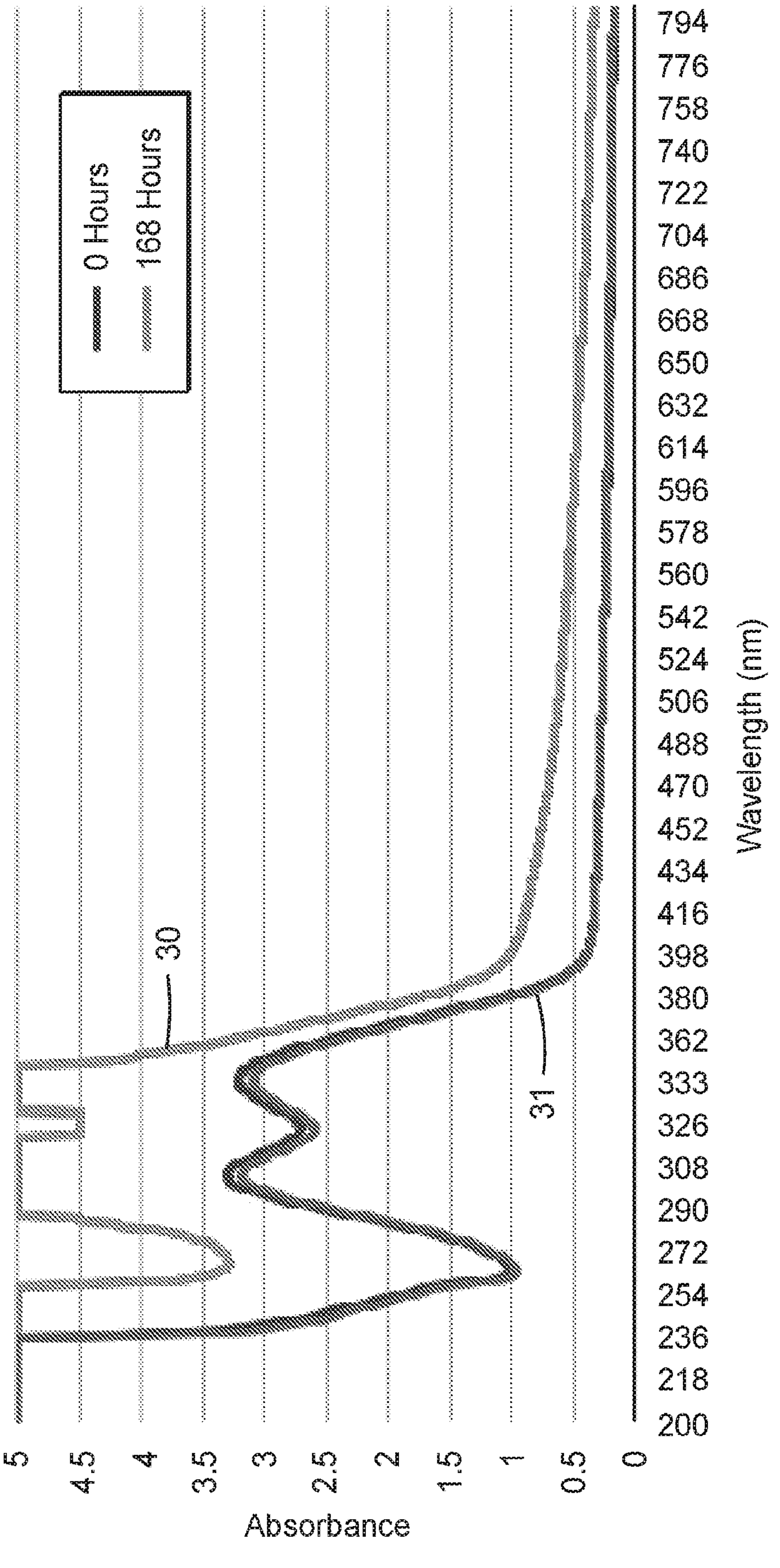
FIG. 2A is a spectral graph of measured light absorbance vs. wavelength as a function of time for the coated film of Comparative Example 1 described herein.

A transparent urethane coating was made with Zirconia nano-particles to absorb UV-C. When exposed to UV-C, the coating degraded and turned yellow in only 168 hour exposure to 222 nm UV-C as shown in FIG. 2A, wherein reference numeral 30 refers to the Absorbance spectrum of the unexposed coating after zero hours of UV-C exposure, and reference numeral 31 refers to the Absorbance spectrum of the coating after 168 hours of exposure.

Comparative Example 2

Figure 2B:
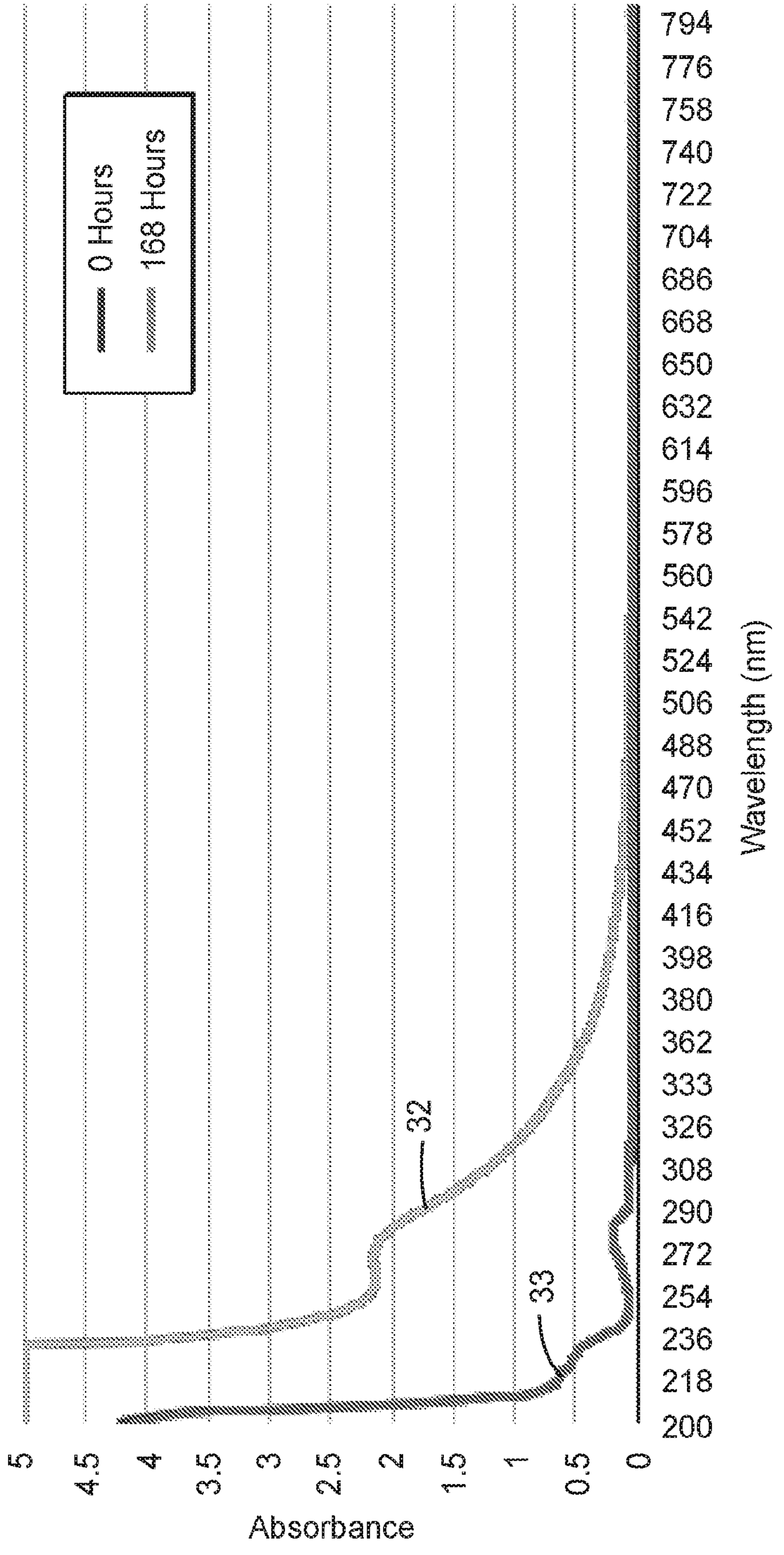
FIG. 2B is a spectral graph of measured light absorbance vs. wavelength as a function of time for the coated film of Comparative Example 2 described herein.

A polyolefin copolymer film sold under the tradename VIVION, available from USI Group (Taiwan), was exposed to UV-C radiation at 254 nm. As shown in FIG. 2B, the loss in light transmission shown as Absorbance in only 168 hour of exposure to 254 nm UV-C radiation was significant and the film rapidly degraded, wherein reference numeral 32 refers to the unexposed film after zero hours of UV-C exposure, and reference numeral 33 refers to the film after 168 hours of UV-C exposure.

Comparative Example 3

Fluoropolymers (available under the trade designation "THV815" and "THV221" from Dyneon LLC (Oakdale, MN) were co-extruded with a 40 mm twin screw extruder and a flat film extrusion die onto a film casting wheel chilled to 21° C. (70° F.) to form a 2 mil (50 micrometers) thick bi-layer fluoropolymer film. 100-micrometer thick fluoropolymer ("THV815") film. The film was heat-sealed to an aluminum sheet at 140° C. with the THV221 fluoropolymer side facing the aluminum sheet. The bi-layer fluoropolymer film could not be peeled from the aluminum sheet.

Substrate Film Example 1

Figure 3A:
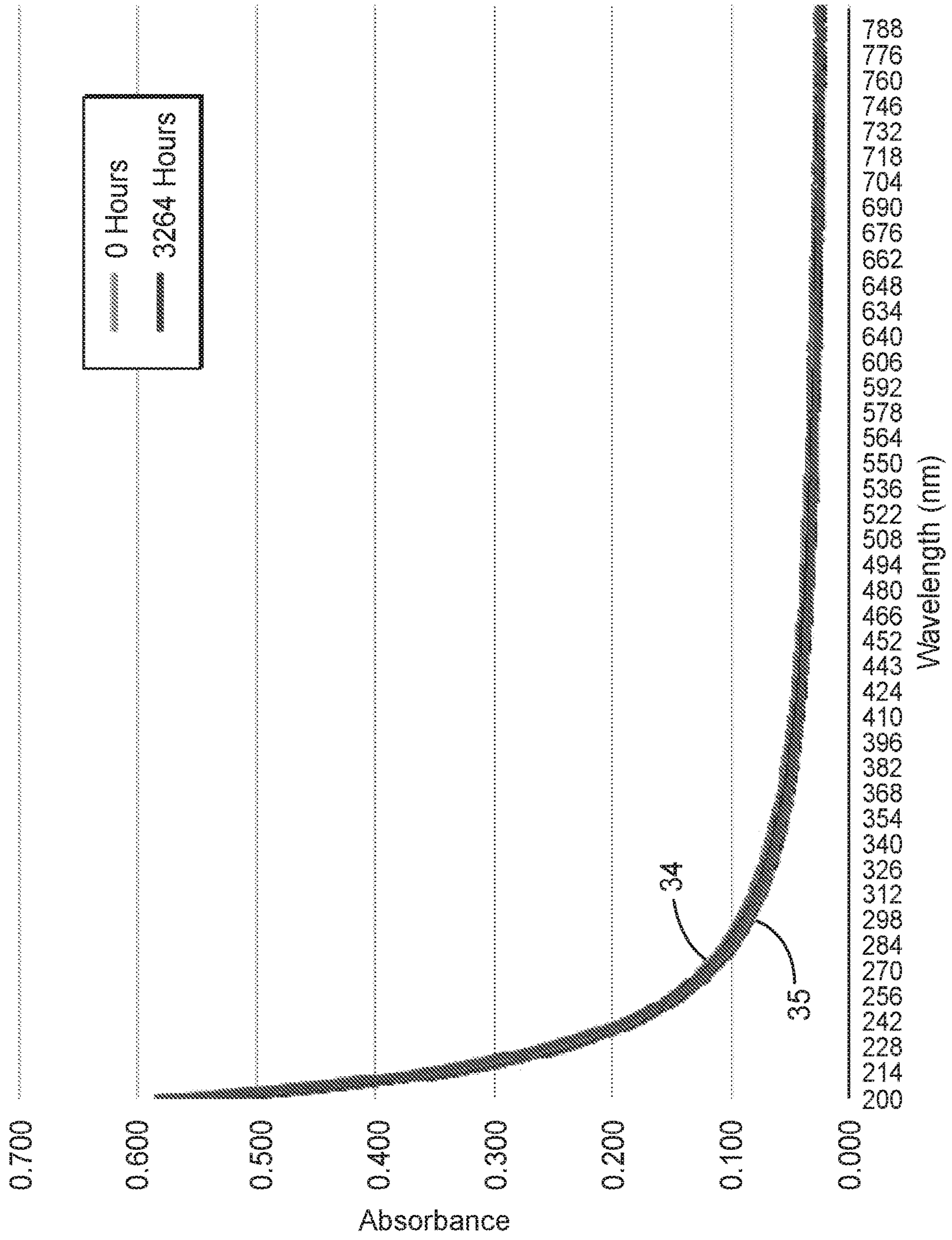
FIG. 3A is a spectral graph of measured light absorbance vs. wavelength as a function of time for the UV-C protective film of Substrate Film Example 1 described herein.

A 4 mil (100 micrometer) thick THV815 film obtained under the trade designation "NOWOFLON THV815" from Nowofol Kunststoffprodukte GmbH KG (Siegsdorf, Germany) was exposed to UV-C radiation at 254 nm for 3264 hour according to the UV-C Service Life Test. The Absorbance spectra are shown in FIG. 3A, wherein reference numeral 34 refers to the unexposed film after zero hours of UV-C exposure, and reference numeral 35 refers to the film after 3264 hours of UV-C exposure.

Figure 3B:
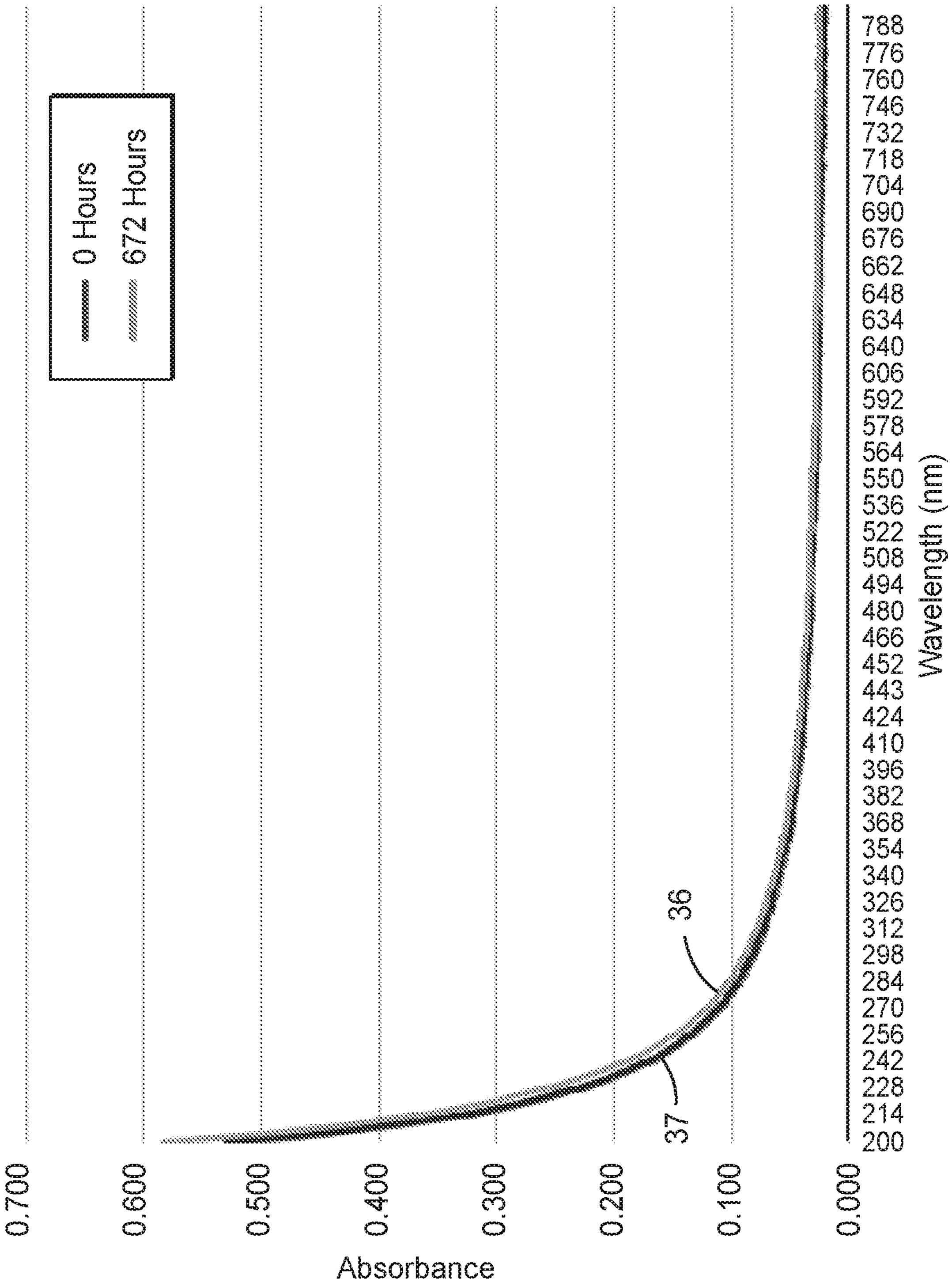
FIG. 3B is another spectral graph of measured light absorbance vs. wavelength as a function of time for the UV-C protective film of Substrate Film Example 1 described herein.

Another sample of this film was likewise exposed to UV-C radiation at 222 nm for 672 hour according to the UV-C Service Life Test. The Absorbance spectra are shown in FIG. 3B, wherein reference numeral 36 refers to the unexposed film after zero hours of UV-C exposure, and reference numeral 37 refers to the film after 672 hours of UV-C exposure. There is no indication of degradation or loss in light transmission. THV815 has a melting point of 225° C. and does not stick to surfaces heated to 150° C.

Substrate Film Example 2

Figure 3C:
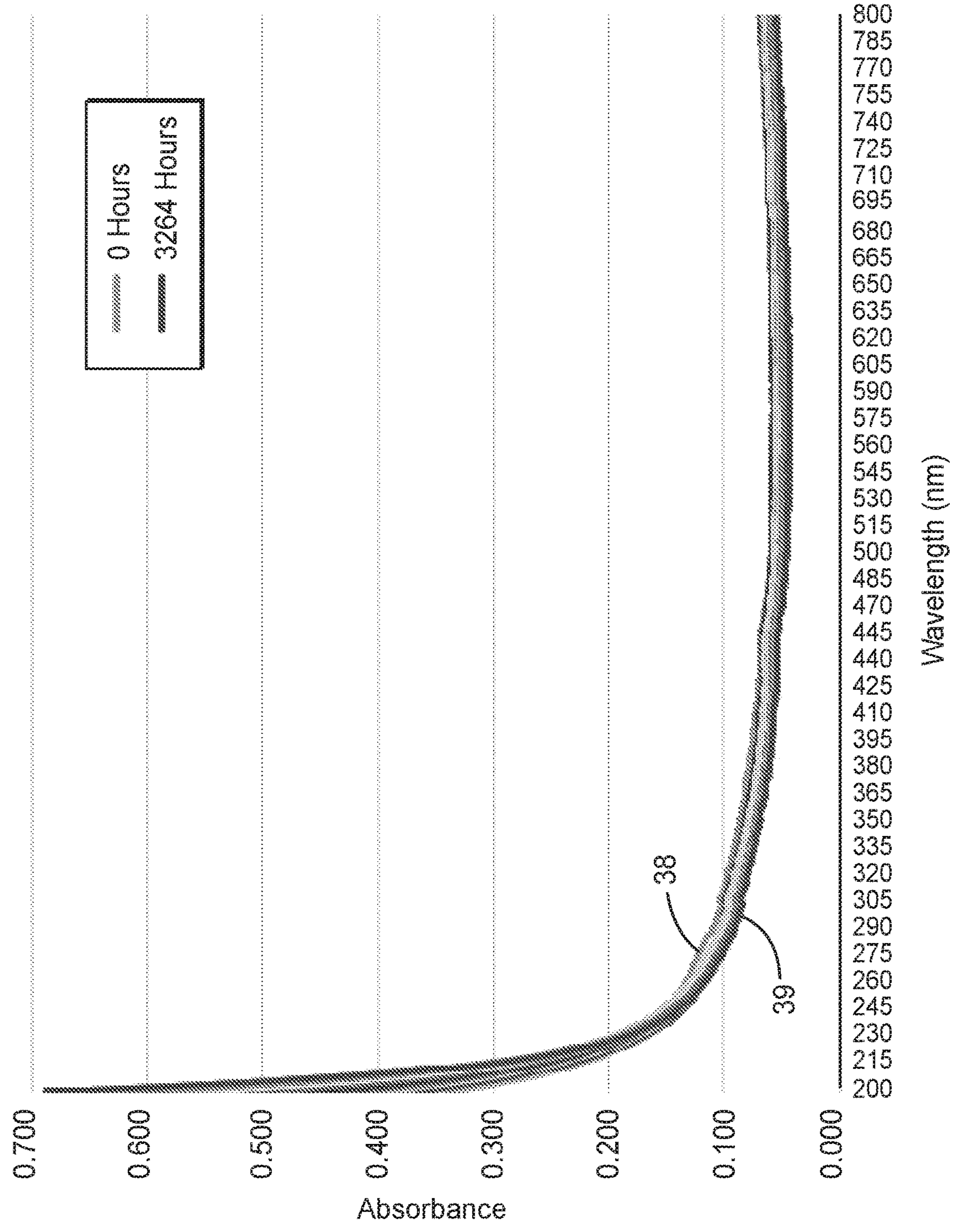
FIG. 3C is a spectral graph of measured light absorbance vs. wavelength as a function of time for the UV-C protective film of Substrate Film Example 2 described herein.

A 12 mil (300 micrometer) thick THV221 film made by 3M Company (St. Paul, MN) was exposed to UV-C radiation at 254 nm for 3264 hour according to the UV-C Service Life Test. The Absorbance spectra are shown in FIG. 3C, wherein reference numeral 38 refers to the unexposed film after zero hours of UV-C exposure, and reference numeral 39 refers to the film after 3264 hours of UV-C exposure. There is no indication of degradation or loss in light transmission. THV221 had a melting point of 130° C. and can be heat sealed at 140° C.

Narrow Band-pass Filter UV-C Mirror Films

Narrow Band-Pass Filter UV-C Mirror Film Example 1

A multi-layer UV-C protective mirror film was made by vapor coating an inorganic optical stack having first optical layers comprising $HfO_2$ and second optical layers comprising $SiO_2$ onto a 100 micrometers (4 mil) thick fluoropolymer film substrate (obtained under the trade designation "NOWOFLON THV815" from Nowofol Kunststoffprodukte GmbH KG (Siegsdorf, Germany). More specifically, a thin film stack comprised of 13 alternating layers of $HfO_2$ and $SiO_2$ and designed to have peak reflectance at 254 nm was prepared using the following method.

The method began by coating layer 1, a 30.00 nm layer of $HfO_2$, using electron beam deposition. In electron beam deposition, a four-hearth evaporation source was used. Each hearth was cone-shaped and 17 cm 3 volume of $HfO_2$ chunks filled it. The magnetically deflected high voltage electron beam was raster scanned over the material surface as filament current of the beam is steadily increased in a pre-programmed fashion.

Upon completion of the pre-programmed step, the $HFO_2$ surface was heated to evaporation temperature, about 2500° C., and a source shutter opened, the $HfO_2$ vapor flux emerging from the source in a cosine-shaped distribution and condensing upon the substrate material above the source. For enhancement of coating uniformity, the substrate holders rotated during deposition. Upon reaching the prescribed coating thickness (30.00 nm) the filament current shut off; the shutter closed and the $HfO_2$ material cooled.

Next, coating layer 2 was deposited directly on coating layer 1. For coating layer 2 the evaporation source was then rotated to a hearth containing chunks of $SiO_2$ and a similar pre-programmed heating process was begun. Here, the $SiO_2$ surface temperature was about 950° C. when the source shutter opened and, upon reaching the prescribed coating thickness (45.02 nm), the filament current shut off; the shutter closed and the $HfO_2$ material cooled.

Figure 4:
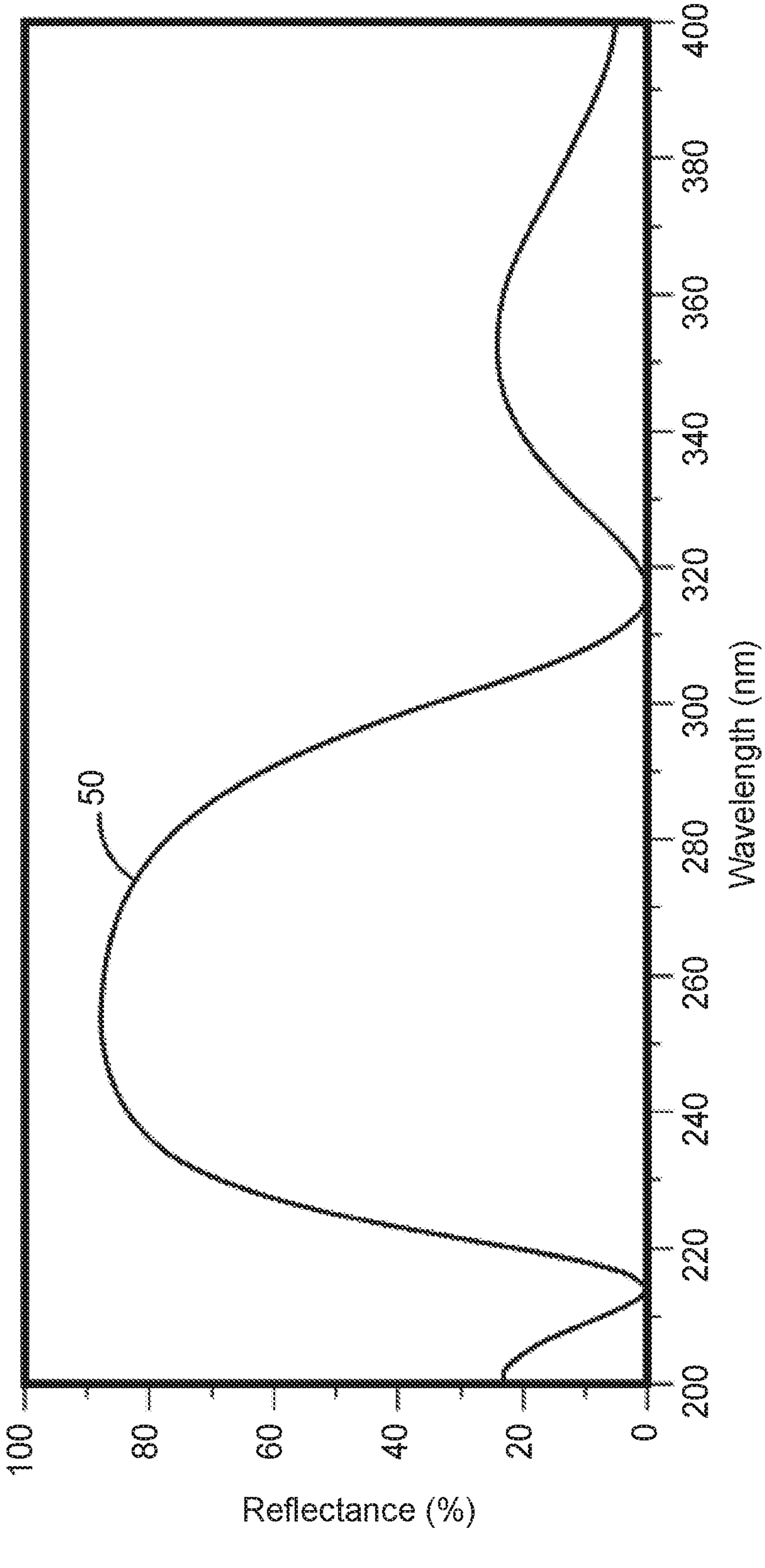
FIG. 4 is a graph of measured light reflectance vs. wavelength for the UV-C protective mirror film of Example 1 described herein.

This step-wise alternating-layer process was continued, layer by layer, until a total number of 13 layers (seven layers of $HfO_2$ and six layers of $SiO_2$) was reached. The Reflectance spectrum of the multi-layer UV-C protective mirror film was measured with a spectrophotometer (obtained under the trade designation "SHIMADZU 2550 UV-VIS" from Shimadzu, Kyoto, Japan). The resulting Reflectance spectrum 50 is shown in FIG. 4.

Modeled Prophetic Example I

Figure 5:
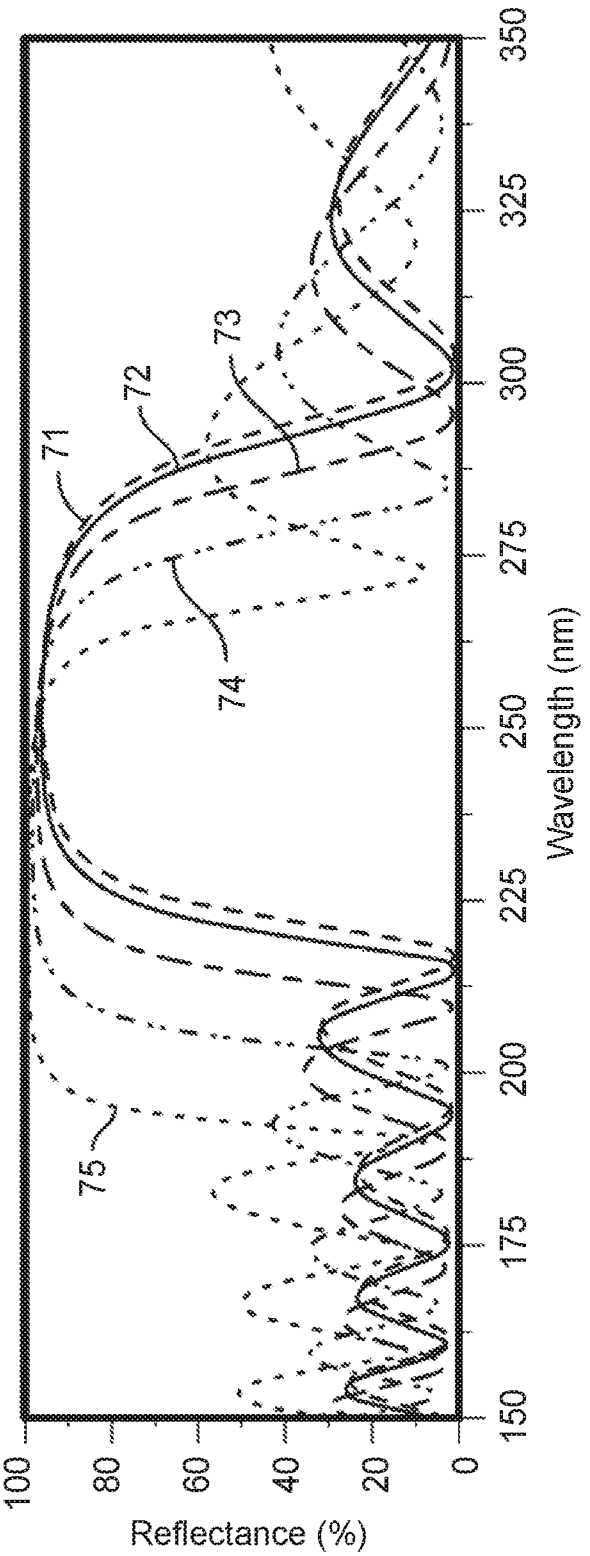
FIG. 5 is a graph of modeled light reflection vs. wavelength for the UV-C protective mirror film of Prophetic Example I described herein.

The Berreman methodology described in the Journal of the Optical Society of America (Volume 62, Number 4, April 1972) and the Journal of Applied Physics (Volume 85, Number 6, March 1999), was used to calculate the % Reflectance spectra shown in FIG. 5 for a multilayer optical film with 14 alternating optical layers of ZrON high refractive index first layers and $SiO_2$ low refractive index second layers for a median reflectance target of 254 nm at normal incident light angle (0°). The % Reflectance spectra were calculated for the prophetic UV-C reflective multilayer optical film for incident light angles of 0° (spectrum 71), 10° (spectrum 72), 20° (spectrum 73), 30° (spectrum 74) and 40° (spectrum 75).

Modeled Prophetic Example II

This UV-C radiation reflective protective film includes a multilayer optical film comprising first optical layers made with PVDF (polyvinylidene fluoride) (available under the trade designation "PVDF 6008" from Dyneon LLC (Oakdale, MN) and second optical layers comprising a fluoropolymer (available under the trade designation "THV815GZ" from Dyneon LLC (Oakdale, MN). The PVDF ("PVDF 6008") and a fluoropolymer ("THV815GZ") can be coextruded through a multilayer melt manifold to form an optical stack of 254 layers.

The layer thickness profile (layer thickness values) of this UV-C radiation reflective protective film can be adjusted to be about a linear profile with the thinnest layers adjusted to have about a ¼ wave optical thickness (refractive index times physical thickness) for 200 nm light and progressing to the thickest layers which were adjusted to be about a ¼ wave optical thickness for 300 nm light when reflection is measured at a 0° incident light angle (normal angle).

Figure 6:
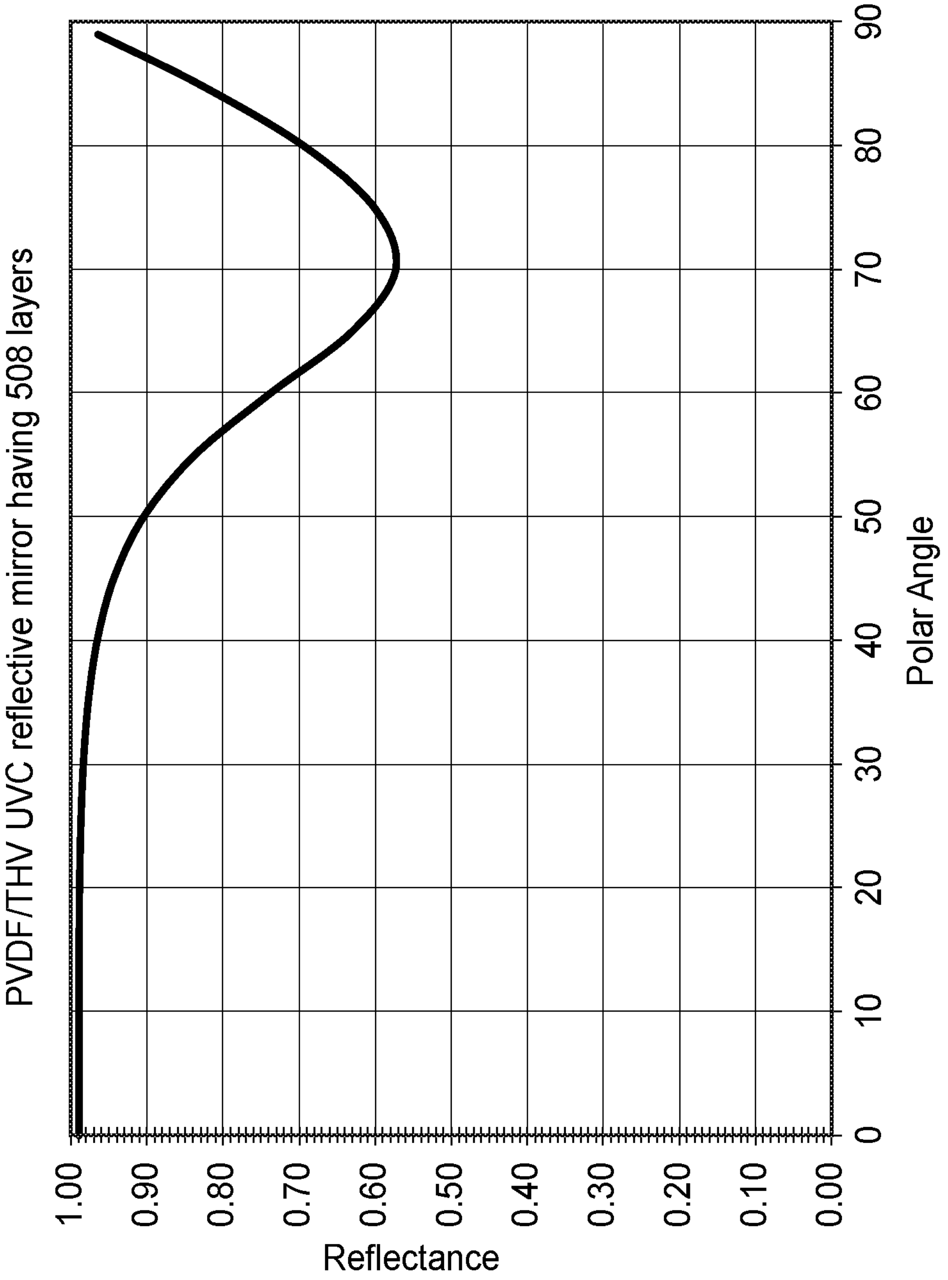
FIG. 6 is a graph of modeled light reflection vs. wavelength for the UV-C protective mirror film of Prophetic Example II described herein.

The Berreman methodology described in the Journal of the Optical Society of America (Volume 62, Number 4, April 1972) and the Journal of Applied Physics (Volume 85, Number 6, March 1999), was used to calculate the % Reflectance spectrum shown in FIG. 6 for a multilayer optical film with a total of 254 layers (127 PVDF high refractive index optical layers and 127 THV815 low refractive index layers, each high index layer alternating with a low index layer) and exhibiting a median reflectance target of 250 nm at a normal incident light angle (0°).

Broad Band-Pass Filter UV-C Mirror Films

Broad Band-pass Filter UV-C (UV-B Reflective [Protective] Mirror Film) Example 2—$ZrO_xN_y$: $SiAl_xO$ A broad band UV-C protective mirror film reflecting over the range 240-310 nm was created by sputter coating an inorganic optical stack having first optical layers comprising $ZrO_xN_y$ and second optical layers comprising $SiAl_xO_y$ onto a 4 mil (100 micrometers) thick fluoropolymer film (obtained under the trade designation "NOWOFLON THV 815" from Nowofol Kunststoffprodukte GmbH & Co. KG Kunststoffprodukte GmbH & Co. KG (Siegsdorf, Germany).

UV transparent films were coated in continuous roll to roll (R2R) fashion, using $ZrO_xN_y$ as the high refractive index material and $SiAl_xO_y$ as the low refractive index material. The optical design was alternating quarter wave thickness layers of the two materials tuned to start reflecting at 240 nm with a gradient of layer thickness, the gradient ending such that 310 nm was reflected at the final thicknesses. For $ZrO_xN_y$, with refractive index at 254 nm of 2.25, the physical thickness target was 24.66 nm. For $SiAl_xO_y$, here sputtered from an aluminum-doped silicon sputter target, with refractive index 1.49, the target thickness was 37.23 nm.

Layer one $ZrO_xN_y$ was DC sputtered from a pure zirconium sputter target in a gas mixture of argon, oxygen and nitrogen. Whereas argon was the primary sputtering gas, oxygen and nitrogen levels were set to achieve transparency, low absorptance and high refractive index. The film roll transport initially started at a pre-determined speed, and the sputter source power was ramped to full operating power, followed by introduction of the reactive gases and then by achieving steady state condition. The sputter source was orthogonal to and wider than the film which was being coated. Upon reaching the desired length of coated film the reactive gases were set to zero and the target was sputtered to obtain a pure Zr surface state.

The film direction was next reversed and silicon (aluminum doped) from a rotary pair of sputter targets had AC frequency (40 kHz) power applied in an argon sputtering atmosphere. Upon reaching steady state, oxygen reactive gas was introduced to provide transparency and low refractive index. At the pre-determined process setting and line speed the second layer was coated over the length which was coated for layer one. The sputter sources were orthogonal to and wider than the film being coated.

After reaching the desired length of coated film the reactive oxygen was removed and the target was sputtered in argon to obtain a pure silicon (aluminum doped) surface state. This stepwise process was continued, layer by layer, until a total number of 9 layers was reached. Resulting peak reflectance was measured to be 95% at 254 nm and the film transmitted 80% of UV-C radiation at 222 nm when measured with a spectrophotometer (obtained under the trade designation "LAMBDA 1050 UV-VIS" from Perkin Elmer Instruments (Waltham, MA).

Broad Band UV-C Band-pass Filter (UV-B+UV-A Reflective [Protective] Mirror Film) Example 3 ($ZrO_xN_y/SiAl_xO_y$)

A broad band UV-C protective mirror film reflecting over the range 240-310 nm was created by sputter coating an inorganic optical stack having first optical layers comprising $ZrO_xN_y$ and second optical layers comprising $SiAl_xO_y$ onto 4 mil (100 micrometers) thick fluoropolymer film (obtained under the trade designation "NOWOFLON THV 815" from Nowofol Kunststoffprodukte GmbH KG (Siegsdorf, Germany).

UV transparent films were coated in continuous roll to roll (R2R) fashion, using $ZrO_xN_y$ as the high refractive index material and $SiAl_xO_y$ as the low refractive index material. The optical design was alternating quarter wave thickness layers of the two materials tuned to start reflecting at 240 nm with a gradient of layer thickness, the gradient ending such that 310 nm was reflected at the final thicknesses. For $ZrO_xN_y$, with refractive index at 254 nm of 2.25, the physical thickness target was 24.66 nm. For $SiAl_xO_y$, here sputtered from an aluminum-doped silicon sputter target, with refractive index 1.49, the target thickness was 37.23 nm.

Layer one $ZrO_xN_y$ was DC sputtered from a pure zirconium sputter target in a gas mixture of argon, oxygen and nitrogen. Whereas argon is the primary sputtering gas, oxygen and nitrogen levels were set to achieve transparency, low absorptance and high refractive index. The film roll transport initially started at a pre-determined speed, and the sputter source power was ramped to full operating power, followed by introduction of the reactive gases and then by achieving steady state condition. The sputter source was orthogonal to and wider than the film which was being coated. Upon reaching the desired length of coated film the reactive gases were set to zero and the target was sputtered to obtain a pure Zr surface state.

The film direction was next reversed and silicon (aluminum doped) from a rotary pair of sputter targets had AC frequency (40 kHz) power applied in an argon sputtering atmosphere. Upon reaching steady state, oxygen reactive gas was introduced to provide transparency and low refractive index. At the pre-determined process setting and line speed the second layer was coated over the length which was coated for layer one. The sputter sources were orthogonal to and wider than the film being coated. After reaching the desired length of coated film the reactive oxygen was removed and the target was sputtered in argon to obtain a pure silicon (aluminum doped) surface state.

This stepwise process was continued, layer by layer, until a total number of 9 layers was reached. Resulting peak reflectance was measured to be 95% at 254 nm when measured with a spectrophotometer ("LAMBDA 1050 UV-VIS").

A UV-B mirror film reflecting over the range 310-360 nm was made by coextruding first optical layers made of PMMA (obtained under the trade designation "PLEXIGLAS V044" from Altuglas International, Arkema Inc. (Bristol, PA) with second optical layers made of fluoropolymer2 (obtained under the trade designation DYNEON THV 221GZ from Dyneon LLC (Oakdale, MN). The PMMA and fluoropolymer 2 were coextruded through a multilayer polymer melt manifold to form a stack of 275 total optical layers.

The layer thickness profile (layer thickness values) of this UV-B Mirror Film was adjusted to be approximately a linear profile with the first (thinnest) optical layers adjusted to have about a quarter wave optical thickness (refractive index times physical thickness) for 310 nm light and progressing to the thickest layers which were adjusted to be about a quarter wave optical thickness for 360 nm light. Layer thickness profile of this film was adjusted to provide for improved spectral characteristics using the axial rod apparatus taught in U.S. Pat. No. 6,783,349 (Neavin et al.), the entire disclosure of which is incorporated herein by reference, combined with layer profile information obtained with atomic force microscopic techniques.

In addition, to these optical layers, non-optical protective skin layers made of PMMA (each of 100 micrometers thickness) were coextruded on either side of the optical stack. This multilayer coextruded melt stream was cast onto a chilled roll at 5.4 meters according to minute creating a multilayer cast web approximately 400 micrometers thick. The multilayer cast web was then preheated for about 10 seconds at 120° C. and biaxially stretched (to orient the film) at draw ratios of 3.0 in each of the machine (down-web) direction and the transverse (cross-web) direction. The UV-B reflective multilayer film was measured with a spectrophotometer (Perkin Elmer "LAMBDA 1050 UV-VIS") to reflect 95% of UV-B radiation over a bandwidth from 310 nm to 360 nm.

A UV-A mirror film reflecting over the range 340-390 nm was made by coextruding first optical layers made of PMMA (obtained under the trade designation "PLEXIGLAS V044" from Altuglas International, Arkema Inc. (Bristol, PA) with second optical layers made of fluoropolymer 2 (obtained under the trade designation "DYNEON THV 221GZ" from Dyneon LLC (Oakdale, MN). The PMMA and fluoropolymer 2 were coextruded through a multilayer polymer melt manifold to form a stack of 275 optical layers.

The layer thickness profile (layer thickness values) of this UV-B Mirror Film was adjusted to be approximately a linear profile with the first (thinnest) optical layers adjusted to have about a quarter wave optical thickness (refractive index times physical thickness) for 340 nm light and progressing to the thickest layers which were adjusted to be about a quarter wave optical thickness for 390 nm light. Layer thickness profile of this film was adjusted to provide for improved spectral characteristics using the axial rod apparatus taught in U.S. Pat. No. 6,783,349 (Neavin et al.), the entire disclosure of which is incorporated herein by reference, combined with layer profile information obtained with atomic force microscopic techniques.

In addition, to these optical layers, non-optical protective skin layers made of PMMA (each of 100 micrometers thickness) were coextruded on either side of the optical stack. This multilayer coextruded melt stream was cast onto a chilled roll at 5.0 meters according to minute creating a multilayer cast web approximately 435 micrometers thick. The multilayer cast web was then preheated for about 10 seconds at 120° C. and biaxially stretched (to orient the film) at draw ratios of 3.0 in each of the machine (down-web) direction and the transverse (cross-web) direction. The UV-A reflective multilayer film was measured with a spectrophotometer (Perkin Elmer "LAMBDA 1050 UV-VIS") to reflect 95% of UV-A radiation over a bandwidth from 340 nm to 390 nm.

Figure 7:
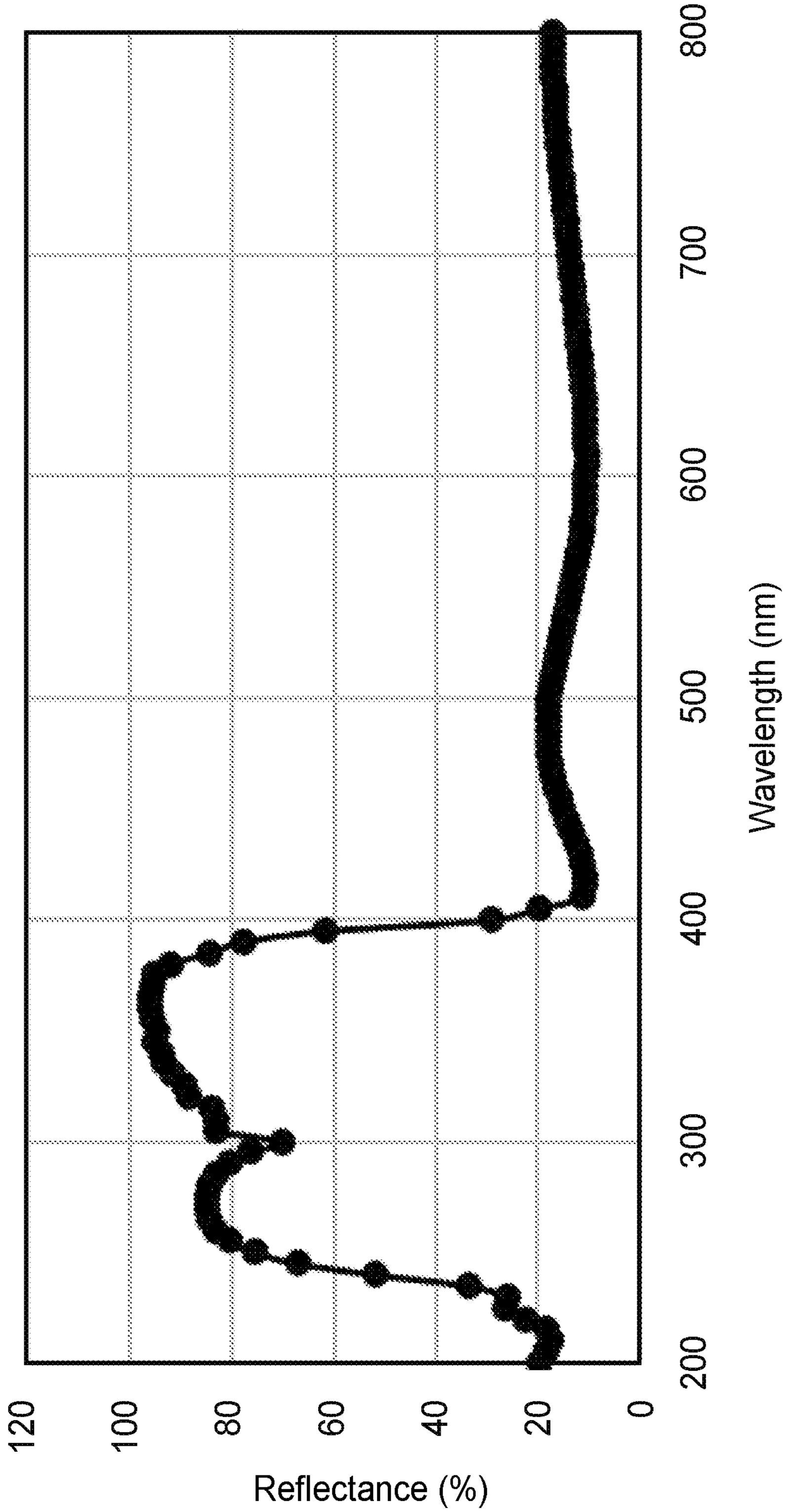
FIG. 7 is a graph of measured light reflectance vs. wavelength for the broadband UV-C protective mirror film of Example 3 described herein.

The 240-310 nm UV-C mirror film, 310-360 nm UV-B mirror film, and 340-390 nm UV-A mirror films were heat laminated in an oven at 130° C. under 5 lbs (2.27 kg) of weight for 2 hour. The heat laminated UV mirror film stack reflectance spectrum was measured with a spectrophotometer (Perkin Elmer "LAMBDA 1050 UV-VIS"). The laminated broad band UV-C protective mirror film exhibited an average % Reflectance of 85% over the wavelength range of 240 nm to 390 nm, as shown by the Reflectance spectrum in FIG. 7.

Broad Band UV-C Band-pass Filter (UV-B+UV-A Reflective [Protective] Mirror Film) Example 4 ($HfO_2$:$SiO_2$/$ZrO_xN_y$:$SiAl_xO_y$)

A broad band UV-C protective mirror film reflecting over the range 215-280 nm was made by vapor coating an inorganic optical stack having first optical layers comprising $HfO_2$ and second optical layers comprising $SiO_2$ onto 100 micrometers (4 mil) thick fluoropolymer film (obtained under the trade designation "NOWOFLON THV 815" from Nowofol Kunststoffprodukte GmbH KG (Siegsdorf, Germany).

More specifically, a thin film stack comprised of alternating layers of $HfO_2$ and $SiO_2$, and designed to have peak reflectance at 254 nm, began by coating layer 1 $HfO_2$ at 30.00 nm. In electron beam deposition, a four-hearth evaporation source was used. Each hearth was cone-shaped and 17 cm 3 volume of $HfO_2$ chunks filled it. A magnetically deflected high voltage electron beam was raster scanned over the material surface as filament current of the beam was steadily, in a pre-programmed fashion, increased.

Upon completion of the pre-programmed step, the $HfO_2$ surface was heated to evaporation temperature, about 2500° C., and a source shutter opened, the $HfO_2$ vapor flux emerged from the source in a cosine-shaped distribution and condensed upon the substrate material above the source. For enhancement of coating uniformity, the substrate holders rotated during deposition. Upon reaching the prescribed coating thickness (30.00 nm) the filament current was shut off; the shutter closed and the $HfO_2$ material cooled.

For layer 2 the evaporation source was then rotated to a hearth containing chunks of $SiO_2$ and a similar pre-programmed heating process began. Here, the $SiO_2$ surface temperature was about 950° C. when the source shutter opened and, upon reaching the prescribed coating thickness (45.02 nm), the filament current was shut off; the shutter closed and the $SiO_2$ material cooled.

This stepwise process was continued, layer by layer, until a total number of 13 layers was reached. Resulting peak reflectance was measured with a spectrophotometer (obtained under the trade designation "SHIMADZU UV-2550 UV-VIS" from Shimadzu Corp. (Kyoto, Japan) and found to be 95% at 222 nm.

Figure 8:
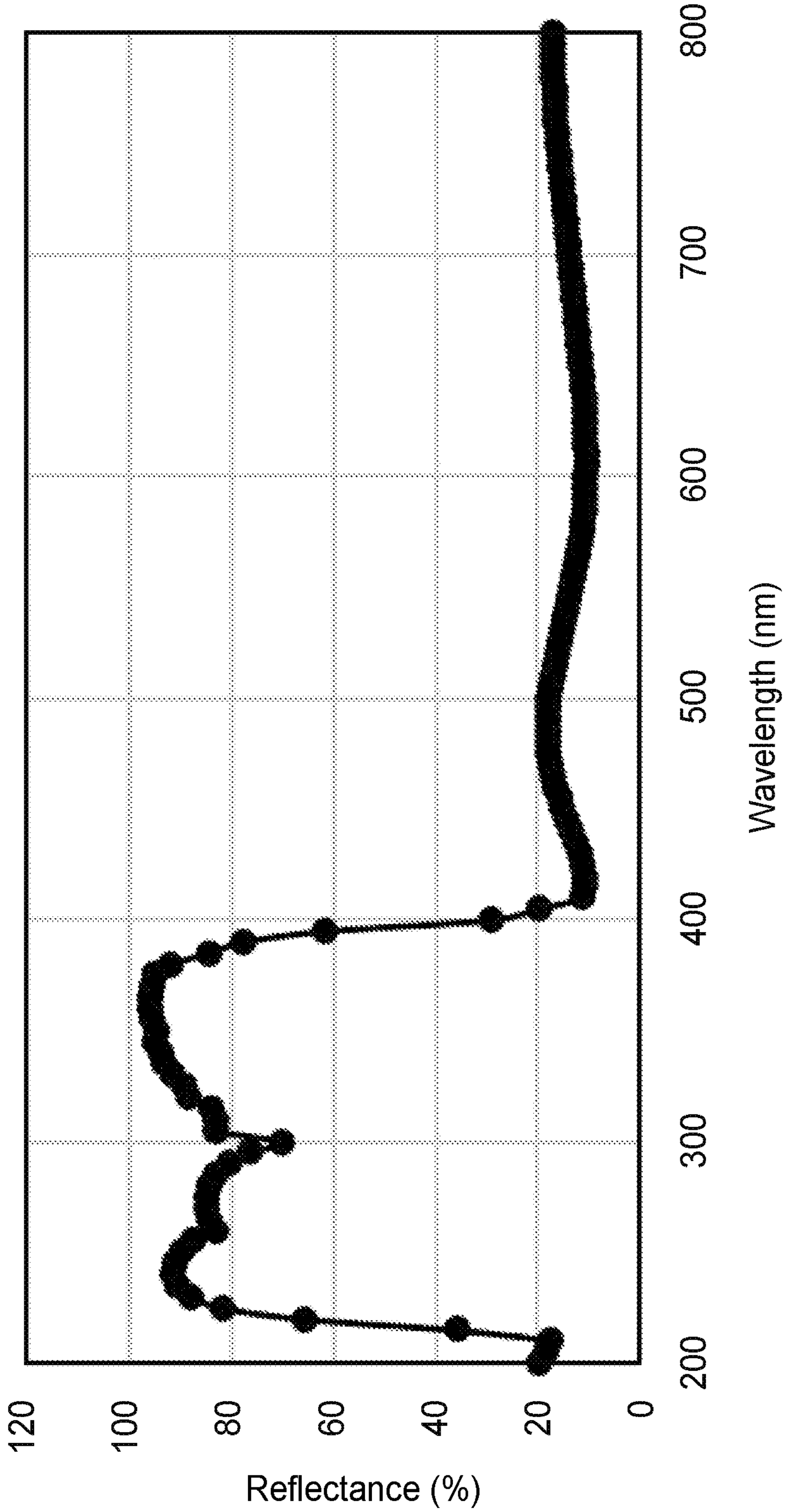
FIG. 8 is a graph of measured light reflectance vs. wavelength for the broadband UV-C protective mirror film of Example 4 described herein.

The UV-C mirror film reflecting over the range 215-280 nm was then heat laminated to the heat laminated UV mirror film stack described in Example 3 in an oven at 130° C. under 5 lbs (2.27 kg) of weight for 2 hour. The laminated broad band UV-C protective mirror film exhibited an average % Reflectance of 85.6% over the wavelength range of 215 nm to 390 nm, as shown by the Reflectance spectrum in FIG. 8.

Modeled Prophetic Example III

A broad band UV-C protective mirror film reflecting over the range 260-390 nm could be made by coextruding first optical layers made of fluoropolymer 1 (available under the trade designation "DYNEON FLUOROPLASTIC PVDF 6008" from Dyneon LLC (Oakdale, MN) with second optical layers made of fluoropolymer 2 (available under the trade designation "DYNEON THV 221GZ" from Dyneon LLC (Oakdale, MN).

The fluoropolymer 1 and fluoropolymer 2 would be coextruded through a multilayer polymer melt manifold to form a stack of 275 optical layers. The layer thickness profile (layer thickness values) of this broad band UV-C Mirror Film would be adjusted to approximately a linear profile with the first (thinnest) optical layers adjusted to have about a quarter wave optical thickness (refractive index times physical thickness) for 260 nm light and progressing to the thickest layers which were adjusted to be about a quarter wave optical thickness for 390 nm light.

Layer thickness profiles of this film would be adjusted to provide for improved spectral characteristics using the axial rod apparatus taught in U.S. Pat. No. 6,783,349 (Neavin et al.), the entire disclosure of which is incorporated herein by reference, combined with layer profile information obtained with atomic force microscopic techniques.

In addition, to these optical layers, non-optical protective skin layers would be made of fluoropolymer1 (each of 100 micrometers thickness) were coextruded on either side of the optical stack. This multilayer coextruded melt stream would be cast onto a chilled roll at 5.4 meters according to minute creating a multilayer cast web approximately 400 micrometers thick.

The multilayer cast web would then be preheated for about 10 seconds at 120° C. and biaxially stretched (to orient the film) at draw ratios of 3.0 in each of the machine (down-web) direction and the transverse (cross-web) direction. The UV reflective multilayer film when measured with a spectrophotometer (Perkin Elmer "LAMBDA 1050 UV-VIS") is expected to reflect 95% of UV light over a bandwidth from 260 nm to 390 nm.

A broad band UV-C mirror film would be made by vapor coating a UV-C film reflecting over the range 210-270 nm and having an inorganic optical stack having first optical layers comprising $HfO_2$ and second optical layers comprising $SiO_2$, onto the 260-390 nm fluoropolymer UV mirror film described above. More specifically, a thin film stack comprised of alternating layers of $HfO_2$ and $SiO_2$ and designed to have peak reflectance at 240 nm began by coating layer 1 $HfO_2$ at 30.00 nm. In electron beam deposition, a four-hearth evaporation source would be used. Each hearth would be cone-shaped and 17 cm 3 volume of $HfO_2$ chunks filled it.

A magnetically deflected high voltage electron beam would be raster scanned over the material surface as filament current of the beam is steadily, in a pre-programmed fashion, increased. Upon completion of the pre-programmed step, the $HfO_2$ surface would be heated to evaporation temperature, about 2500° C., and a source shutter opened, the $HfO_2$ vapor flux emerging from the source in a cosine-shaped distribution and condensing upon the substrate material above the source. For enhancement of coating uniformity, the substrate holders rotated during deposition.

Upon reaching the prescribed coating thickness (30.00 nm) the filament current would be shut off; the shutter would be closed and the $HfO_2$ material would be cooled. For layer 2 the evaporation source would then be rotated to a hearth containing chunks of $SiO_2$ and a similar pre-programmed heating process begins. Here, the $SiO_2$ surface temperature would be about 950° C. when the source shutter would be opened and, upon reaching the prescribed coating thickness (45.02 nm), the filament current would be shut off; the shutter would be closed and the $SiO_2$ material would be cooled.

This stepwise process would be continued, layer by layer, until a total number of 13 layers would be reached. The resulting peak reflectance would be measured with a spectrophotometer (obtained under the trade designation "SHIMADZU UV-2550 UV-VIS" from Shimadzu Corp. (Kyoto, Japan) and would be expected to reflect at least 90% of UV light over a bandwidth of 210 nm to 390 nm.

Modeled Prophetic Example IV

A broad band UV-C protective mirror film reflecting over the range 240-390 nm could be made by coextruding first optical layers made of fluoropolymer 1 (available under the trade designation "DYNEON FLUOROPOLYMER PVDF 6008" from Dyneon LLC (Oakdale, MN) with second optical layers made of fluoropolymer 3 (available under the trade designation "DYNEON THV 815GZ" from Dyneon LLC (Oakdale, MN).

The fluoropolymer 1 and fluoropolymer 3 would be coextruded through a multilayer polymer melt manifold to form a stack of 550 optical layers. The layer thickness profile (layer thickness values) of this UV-C Mirror Film would be adjusted to approximately a linear profile with the first (thinnest) optical layers adjusted to have about a quarter wave optical thickness (refractive index times physical thickness) for 240 nm light and progressing to the thickest layers which were adjusted to be about a quarter wave optical thickness for 390 nm light.

Layer thickness profiles of this film would be adjusted to provide for improved spectral characteristics using the axial rod apparatus taught in U.S. Pat. No. 6,783,349 (Neavin et al.), the entire disclosure of which is incorporated herein by reference, combined with layer profile information obtained with atomic force microscopic techniques.

In addition, to these optical layers, non-optical protective skin layers would be made of fluoropolymer1 (each of 100 micrometers thickness) would be coextruded on either side of the optical stack. This multilayer coextruded melt stream would be cast onto a chilled roll at 5.4 meters according to minute creating a multilayer cast web approximately 400 micrometers thick. The multilayer cast web would then be preheated for about 10 seconds at 120° C. and biaxially stretched (to orient the film) at draw ratios of 3.0 in each of the machine (down-web) direction and the transverse (cross-web) direction.

The broad band UV-C reflective multilayer film when measured with a spectrophotometer (Perkin Elmer "LAMBDA 1050 UV-VIS") is expected to reflect 99% of UV light over a wavelength bandwidth from 240 nm to 390 nm and transmit greater than 80% of UV light over a wavelength bandwidth from 215 nm to 230 nm.

Example 5

A UV-C mirror film reflecting over the range 240-310 nm was created by sputter coating an inorganic optical stack having first optical layers comprising $ZrO_xN_y$ and second optical layers comprising $SiAl_xO_y$ onto 100 micrometers (4 mil) thick fluoropolymer film (obtained under the trade designation "NOWOFLON THV 815" from Nowofol Kunststoffprodukte GmbH & Co. KG, Siegsdorf, Germany). Visible light transparent UV-C mirror films were coated in continuous roll to roll (R2R) fashion, using $ZrO_xN_y$ as the high refractive index material and $SiAl_xO_y$ as the low refractive index material.

The optical design was alternating quarter wave thickness layers of the two materials tuned to start reflecting at 240 nm with a gradient of layer thickness, the gradient ending such that 310 nm was reflected at the final thicknesses. For $ZrO_xN_y$, with refractive index at 254 nm of 2.25, the physical thickness target was 24.66 nm. For $SiAl_xO_y$, here sputtered from an aluminum-doped silicon sputter target, with refractive index 1.49, the target thickness was 37.23 nm. Layer one $ZrO_xN_y$ was DC sputtered from a pure zirconium sputter target in a gas mixture of argon, oxygen and nitrogen. Whereas argon was the primary sputtering gas, oxygen and nitrogen levels were set to achieve transparency, low absorptance and high refractive index.

The film roll transport initially started at a pre-determined speed, and the sputter source power was ramped to full operating power, followed by introduction of the reactive gases and then by achieving steady state condition. The sputter source was orthogonal to and wider than the film which was being coated. Upon reaching the desired length of coated film the reactive gases were set to zero and the target was sputtered to obtain a pure Zr surface state.

The film direction was next reversed and silicon (aluminum doped) from a rotary pair of sputter targets had AC frequency (40 kHz) power applied in an argon sputtering atmosphere. Upon reaching steady state, oxygen reactive gas was introduced to provide transparency and low refractive index. At the pre-determined process setting and line speed the second layer was coated over the length which was coated for layer one. The sputter sources were orthogonal to and wider than the film being coated. After reaching the desired length of coated film the reactive oxygen was removed and the target was sputtered in argon to obtain a pure silicon (aluminum doped) surface state.

This stepwise process was continued, layer by layer, until a total number of 9 layers was reached. Resulting peak reflectance was measured to be 95% at 254 nm and the film transmitted 80% of UV-C radiation at 222 nm when measured with a spectrophotometer (obtained under the trade designation "LAMBDA 1050 UV-VIS" from PerkinElmer, Waltham, MA).

Comparative Example 4

An 8 cm wide×16 cm long printed circuit board was fabricated having six 265 nm UV-C LEDs available from Crystal IS that were spaced apart by 2.5 cm in the width direction and 5 cm in the length direction as shown in FIG. 1. A prototype "control" box was fabricated with poster foam board (available from Office Depot (Maplewood, MN) have interior dimensions of 8 cm wide×16 cm long and 1 cm depth and exterior dimensions of 10 cm wide×18 cm long×2 cm depth. Two 1.5 cm diameter holes were drilled in the bottom of the prototype box for UV-C intensity measurements with a ThorLabs UV-C radiometer. One of the holes in the bottom of the prototype box was positioned directly under one of the UV-C LEDs and the other hole was centered between the UV-C LEDs.

With 40 mA of power supplied to each of the LEDs, the Thorlabs sensor measured a UV-C intensity at 265 nm of 119 microWatts directly below one of the UV-C LEDs. With 40 mA of power supplied to each of the LEDs, the Thorlabs sensor measured 9.6 microWatts when centered between the LEDs.

Example 6

A similar prototype box to Comparative Example 4 was fabricated and the UV-C Mirror Film described in Example 5 was attached to the interior surfaces with optically clear adhesive OCA8171 (available from 3M Company) as shown in FIG. 2. UV-C Mirror Film described in Example 5 was also attached to the flat spaces on the printed circuit board between the UV-C LEDs with OCA8171.

With 40 mA of power supplied to each of the LEDs, the Thorlabs sensor measured a UV-C intensity at 265 nm of 118 microWatts directly below one of the UV-C LEDs. With 40 mA of power supplied to each of the LEDs, the Thorlabs sensor measured 33 microWatts when centered between the LEDs.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about."

Furthermore, all publications and patents referenced herein are incorporated by reference in their entirety to the same extent as if each individual publication or patent was specifically and individually indicated to be incorporated by reference. In the event of inconsistencies or contradictions between portions of the incorporated references and this application, the information in the preceding description Various exemplary embodiments have been described. These and other embodiments are within the scope of the following claims.

What is claimed is:

1. A device comprising:

a housing that is substantially impermeable to ultraviolet radiation having a wavelength of from 280 nm to 400 nm, and at least one window defined in the housing, wherein the window comprises a UV-C radiation band-pass mirror film comprised of a plurality of alternating first and second optical layers collectively transmitting UV-C radiation at a wavelength from 190 nm to 230 nm and does not substantially transmit UV-A and UV-B radiation at a wavelength of from 280 nm to 400 nm; and an ultraviolet radiation source positioned within the housing, wherein the ultraviolet radiation source is capable of emitting ultraviolet radiation at one or more wavelengths from 100 nm to 400 nm; the device optionally further comprising:

an ultraviolet mirror film attached to the housing so as to reflect ultraviolet radiation emitted by the ultraviolet radiation source, wherein the ultraviolet mirror film is comprised of at least a plurality of alternating first and second optical layers collectively reflecting at least 50, 60, 70, 80, 90, or 95 percent of incident UV-C ultraviolet radiation in a wavelength range from 190 nm to 230 nm, and collectively transmitting at least 50, 60, 70, 80, 90, or 95 percent of incident ultraviolet radiation in a wavelength range from greater than 230 nm to 400 nm, wherein at least 50, 60, 70, 80, 90, or 95 percent of ultraviolet radiation having a wavelength between at least 230 nm and 400 nm transmitted through the ultraviolet mirror film is absorbed by the housing.

2. The device of claim 1, wherein the housing comprises a hollow nonplanar shape, further wherein the ultraviolet radiation source is substantially surrounded by the housing.

3. The device of claim 1, wherein the ultraviolet radiation source is a low-pressure mercury lamp, a medium pressure mercury lamp, a deuterium arc lamp, a xenon arc lamp, a germicidal lamp, or an excimer lamp.

4. The device of claim 1, wherein the UV-C radiation band-pass mirror film comprises at least a first optical layer comprising at least one of zirconium oxynitride, hafnia, alumina, magnesium oxide, yttrium oxide, lanthanum fluoride, or neodymium fluoride and at least a second optical layer comprising at least one of silica, aluminum fluoride, magnesium fluoride, calcium fluoride, silica alumina oxide, or alumina doped silica.

5. The device of claim 4, wherein the at least first optical layer comprises at least one of polyvinylidene fluoride or polyethylene tetrafluoroethylene and wherein the at least second optical layer comprises fluorinated ethylene propylene (FEP) or a copolymer of tetrafluoroethylene, hexafluoropropylene, and vinylidene fluoride.

6. The device of claim 1, wherein the ultraviolet mirror film is separated from the ultraviolet radiation source by an air gap.

7. The device of claim 1, wherein the ultraviolet mirror film comprises:

a substrate comprised of a fluoropolymer;

a multilayer optical film disposed on a surface of the substrate, wherein the multilayer optical film is comprised of at least a plurality of alternating first and second optical layers collectively reflecting incident ultraviolet radiation over at least a 30-nanometer wavelength reflection bandwidth in a wavelength range from at least 100 nanometers to 400 nanometers or optionally in a wavelength range from at least 180 to less than 280 nm; and optionally an adhesive layer disposed on a surface of the ultraviolet mirror film.

8. The device of claim 7, wherein the fluoropolymer is a (co) polymer comprising tetrafluoroethylene, hexafluoropropylene, vinylidene fluoride, a perfluoroalkoxy alkane, or a combination thereof.

9. The device of claim 7, wherein the at least first optical layer of the multilayer optical film comprises at least one polyethylene (co) polymer, and wherein the second optical layer of the multilayer optical film comprises at least one fluoropolymer selected from a tetrafluoroethylene (co) polymer, a hexafluoropropylene (co) polymer, a vinylidene fluoride (co) polymer, a hexafluoropropylene (co) polymer, a perfluoroalkoxy alkane (co) polymer, or a combination thereof, optionally wherein the at least one fluoropolymer is crosslinked.

10. The device of claim 7, wherein the at least first optical layer of the multilayer optical film comprises at least one of zirconium oxynitride, hafnia, alumina, magnesium oxide, yttrium oxide, lanthanum fluoride, or neodymium fluoride and wherein the second optical layer of the multilayer optical film comprises at least one of silica, aluminum fluoride, magnesium fluoride, calcium fluoride, silica alumina oxide or alumina doped silica.

11. The device of claim 7, wherein the at least first optical layer of the multilayer optical film comprises at least one of polyvinylidene fluoride or polyethylene tetrafluoroethyne and wherein the second optical layer of the multilayer optical film comprises a copolymer of tetrafluoroethylene, hexafluoropropylene, and vinylidene fluoride.

12. The device of claim 7, wherein the adhesive layer is present and positioned adjacent to the housing, further wherein the adhesive layer comprises a (co) polymer.

13. The device of claim 12, wherein the adhesive layer further comprises an ultraviolet radiation absorber selected from a benzotriazole compound, a benzophenone compound, a triazine compound, or a combination thereof.

14. A method of disinfecting at least one material, the method comprising:

providing the device of claim 1;

directing ultraviolet radiation emitted by the ultraviolet radiation source through the UV-C band-pass mirror film; and exposing the at least one material to the ultraviolet radiation passing through the UV-C band pass mirror film for a time sufficient to achieve a desired degree of disinfection of the at least one material, wherein the ultraviolet radiation passing through the UV-C band-pass mirror film is in a wavelength range from 190 nm to 230 nm, and does not substantially include UV-A and UV-B radiation at a wavelength of from 280 nm to 400 nm, optionally wherein exposing the at least one material to the ultraviolet radiation passing through the UV-C band-pass mirror film is performed until achievement of a log 2, log 3, log 4, or greater reduction in an amount of at least one microorganism present on or in the at least one material, as compared to an amount of the at least one microorganism present prior to exposing the at least one material to the ultraviolet radiation passing through the UV-C band-pass mirror film.

* * * * *